(12) United States Patent
Blackmon

(10) Patent No.: US 12,201,148 B2
(45) Date of Patent: Jan. 21, 2025

(54) CLOSED SYSTEM CAPSULE WITH AIRFLOW, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventor: Zack W. Blackmon, Williamsburg, VA (US)

(73) Assignee: Altria Client Services LLC, Richmond, VA (US)

( * ) Notice: Subject to any disclaimer, the term of this patent is extended or adjusted under 35 U.S.C. 154(b) by 619 days.

(21) Appl. No.: 17/151,317

(22) Filed: Jan. 18, 2021

(65) Prior Publication Data
US 2022/0225671 A1    Jul. 21, 2022

(51) Int. Cl.
| A24F 40/42 | (2020.01) |
| A24F 40/20 | (2020.01) |
| A24F 40/46 | (2020.01) |
| A24F 40/485 | (2020.01) |
| A61M 15/00 | (2006.01) |

(52) U.S. Cl.
CPC .............. *A24F 40/42* (2020.01); *A24F 40/20* (2020.01); *A24F 40/46* (2020.01); *A24F 40/485* (2020.01); *A61M 15/003* (2014.02); *A61M 15/009* (2013.01); *A61M 2205/3653* (2013.01)

(58) Field of Classification Search
CPC .......... A24F 40/00; A24F 40/42; A24F 40/10; A24F 40/20; A24F 40/40; A24F 40/485; A24F 40/46
See application file for complete search history.

(56) References Cited

U.S. PATENT DOCUMENTS

| 855,984 A | 6/1907 | Russell |
| 1,071,389 A | 8/1913 | Blosser |
| 1,934,887 A | 11/1933 | Robinson |
| 4,214,146 A | 7/1980 | Schimanski |
| 4,564,748 A | 1/1986 | Gupton |

(Continued)

FOREIGN PATENT DOCUMENTS

| CN | 103945716 A | 7/2014 |
| CN | 203986136 U | 12/2014 |

(Continued)

OTHER PUBLICATIONS

Crafty Vaporizer manual (2014).

(Continued)

*Primary Examiner* — Christopher M Rodd
*Assistant Examiner* — Daniel Edward Vakili
(74) *Attorney, Agent, or Firm* — Harness, Dickey & Pierce, P.L.C.

(57) ABSTRACT

A capsule for an aerosol-generating device includes a housing. The housing includes an inner frame defining an opening. The housing defines at least one air inlet and at least one air outlet. The capsule also includes an aerosol-forming substrate at least partially within the opening, and a heater supported by the inner frame and extending across at least a portion of the opening. The at least one air inlet, the opening, and the at least one air outlet collectively form at least one airflow pathway through the capsule. The airflow pathway is longer than a thickness of the capsule.

18 Claims, 17 Drawing Sheets

(56) References Cited

U.S. PATENT DOCUMENTS

| | | |
|---|---|---|
| 4,947,874 A | 8/1990 | Brooks et al. |
| 5,388,572 A | 2/1995 | Mulhauser et al. |
| 5,388,573 A | 2/1995 | Mulhauser et al. |
| 5,441,060 A | 8/1995 | Rose et al. |
| 5,460,173 A | 10/1995 | Mulhauser et al. |
| 5,593,792 A | 1/1997 | Farrier et al. |
| 5,619,984 A | 4/1997 | Hodson et al. |
| 5,645,050 A | 7/1997 | Zierenberg et al. |
| 5,665,262 A | 9/1997 | Hajaligol et al. |
| 5,823,182 A | 10/1998 | Van Oort |
| 6,006,747 A | 12/1999 | Eisele et al. |
| 6,065,472 A | 5/2000 | Anderson et al. |
| 6,095,153 A | 8/2000 | Kessler et al. |
| 7,186,958 B1 | 3/2007 | Nelson |
| 7,997,280 B2 | 8/2011 | Rosenthal |
| 8,488,952 B2 | 7/2013 | Landry |
| 8,490,627 B2 | 7/2013 | Levin et al. |
| 8,714,150 B2 | 5/2014 | Alelov |
| 8,910,630 B2 | 12/2014 | Todd |
| 9,481,437 B2 | 11/2016 | Achiwa et al. |
| 9,693,587 B2 | 7/2017 | Plojoux et al. |
| 9,775,379 B2 | 10/2017 | Davidson et al. |
| 9,943,114 B2 | 4/2018 | Batista |
| 10,172,390 B2 | 1/2019 | Nakano et al. |
| 10,179,215 B2 | 1/2019 | Raichman |
| 10,247,443 B2 | 4/2019 | Flick |
| 10,271,578 B2 | 4/2019 | John et al. |
| 10,291,543 B1 | 5/2019 | Felstaine et al. |
| 10,292,436 B2 | 5/2019 | Cirillo et al. |
| 10,328,443 B2 | 6/2019 | Ricketts et al. |
| 10,602,776 B2 | 3/2020 | Batista |
| 2004/0159322 A1 | 8/2004 | Kladders et al. |
| 2005/0063686 A1 | 3/2005 | Whittle et al. |
| 2007/0045288 A1 | 3/2007 | Nelson |
| 2007/0102013 A1 | 5/2007 | Adams et al. |
| 2008/0073558 A1 | 3/2008 | Howell et al. |
| 2009/0293888 A1 | 12/2009 | Williams et al. |
| 2009/0293892 A1 | 12/2009 | Williams et al. |
| 2010/0012118 A1 | 1/2010 | Storz |
| 2010/0059070 A1 | 3/2010 | Potter et al. |
| 2010/0078022 A1 | 4/2010 | Striebig et al. |
| 2010/0139655 A1 | 6/2010 | Genosar et al. |
| 2010/0313901 A1 | 12/2010 | Fernando et al. |
| 2011/0126848 A1 | 6/2011 | Zuber et al. |
| 2011/0192399 A1 | 8/2011 | Wilke et al. |
| 2012/0304990 A1 | 12/2012 | Todd |
| 2012/0325227 A1 | 12/2012 | Robinson et al. |
| 2013/0032145 A1 | 2/2013 | Adler et al. |
| 2013/0186392 A1 | 7/2013 | Haartsen et al. |
| 2013/0233309 A1 | 9/2013 | Todd |
| 2013/0233312 A1 | 9/2013 | Cohn |
| 2013/0255702 A1 | 10/2013 | Griffith, Jr. et al. |
| 2013/0276799 A1 | 10/2013 | Davidson et al. |
| 2014/0041655 A1 | 2/2014 | Barron et al. |
| 2014/0060554 A1 | 3/2014 | Collett et al. |
| 2014/0186015 A1 | 7/2014 | Breiwa, III et al. |
| 2014/0217197 A1 | 8/2014 | Selby et al. |
| 2014/0238423 A1 | 8/2014 | Tucker et al. |
| 2014/0299141 A1 | 10/2014 | Flick |
| 2014/0321837 A1 | 10/2014 | Flick |
| 2014/0345606 A1 | 11/2014 | Talon |
| 2014/0366609 A1 | 12/2014 | Beck et al. |
| 2015/0057811 A1 | 2/2015 | Fan et al. |
| 2015/0059747 A1 | 3/2015 | Von Schuckmann |
| 2016/0021932 A1 | 1/2016 | Silvestrini et al. |
| 2016/0143358 A1 | 5/2016 | Zhu |
| 2016/0295922 A1 | 10/2016 | John et al. |
| 2016/0331913 A1 | 11/2016 | Bourque |
| 2016/0338410 A1 | 11/2016 | Batista et al. |
| 2016/0345630 A1 | 12/2016 | Mironov et al. |
| 2017/0055584 A1 | 3/2017 | Blandino et al. |
| 2017/0071251 A1 | 3/2017 | Goch |
| 2017/0095624 A1 | 4/2017 | Davidson et al. |
| 2017/0119979 A1 | 5/2017 | Davidson et al. |
| 2017/0143041 A1 * | 5/2017 | Batista .................. A24F 1/00 |
| 2017/0143042 A1 | 5/2017 | Batista et al. |
| 2017/0144827 A1 | 5/2017 | Batista |
| 2017/0164657 A1 | 6/2017 | Batista |
| 2017/0196262 A1 | 7/2017 | Brereton et al. |
| 2017/0311648 A1 | 11/2017 | Gill et al. |
| 2018/0007960 A1 | 1/2018 | Suzuki et al. |
| 2018/0084831 A1 | 3/2018 | Mironov |
| 2018/0104214 A1 | 4/2018 | Raichman |
| 2018/0116291 A1 | 5/2018 | Monsees et al. |
| 2018/0214645 A1 | 8/2018 | Reevell |
| 2018/0235279 A1 | 8/2018 | Wilke et al. |
| 2018/0242644 A1 | 8/2018 | Bessant et al. |
| 2018/0263286 A1 | 9/2018 | Reevell |
| 2018/0295885 A1 | 10/2018 | Rojo-Calderon et al. |
| 2018/0361334 A1 | 12/2018 | Bahabri |
| 2019/0117915 A1 | 4/2019 | Raichman |
| 2019/0208823 A1 | 7/2019 | Raichman |
| 2019/0224430 A1 | 7/2019 | Raichman |
| 2020/0229509 A1 | 7/2020 | Griscik et al. |
| 2021/0401047 A1 * | 12/2021 | Van Lancker .......... A24F 40/51 |

FOREIGN PATENT DOCUMENTS

| | | | |
|---|---|---|---|
| CN | 104349687 A | 2/2015 | |
| EP | 0525720 A1 | 2/1993 | |
| EP | 1007124 A1 | 6/2000 | |
| EP | 1029451 A1 | 8/2000 | |
| EP | 1385595 A2 | 2/2004 | |
| EP | 1504768 A1 | 2/2005 | |
| EP | 3644974 A1 | 5/2020 | |
| KR | 101319228 B1 | 10/2013 | |
| RU | 2536115 C2 | 12/2014 | |
| WO | WO-2003/037306 A2 | 5/2003 | |
| WO | WO-2015/116934 A1 | 8/2015 | |
| WO | WO-2016/001921 A2 | 1/2016 | |
| WO | WO-2016/001922 A1 | 1/2016 | |
| WO | WO-2016/001923 A2 | 1/2016 | |
| WO | WO-2016/001924 A2 | 1/2016 | |
| WO | WO-2016/001925 A1 | 1/2016 | |
| WO | WO-2016/001926 A1 | 1/2016 | |
| WO | WO2016/005533 A1 * | 1/2016 | ............ A24F 47/00 |
| WO | WO-2016/026219 A1 | 2/2016 | |

OTHER PUBLICATIONS

International Search Report and Written Opinion thereof dated Mar. 30, 2022 for corresponding International Application No. PCT/US2021/060633.

* cited by examiner

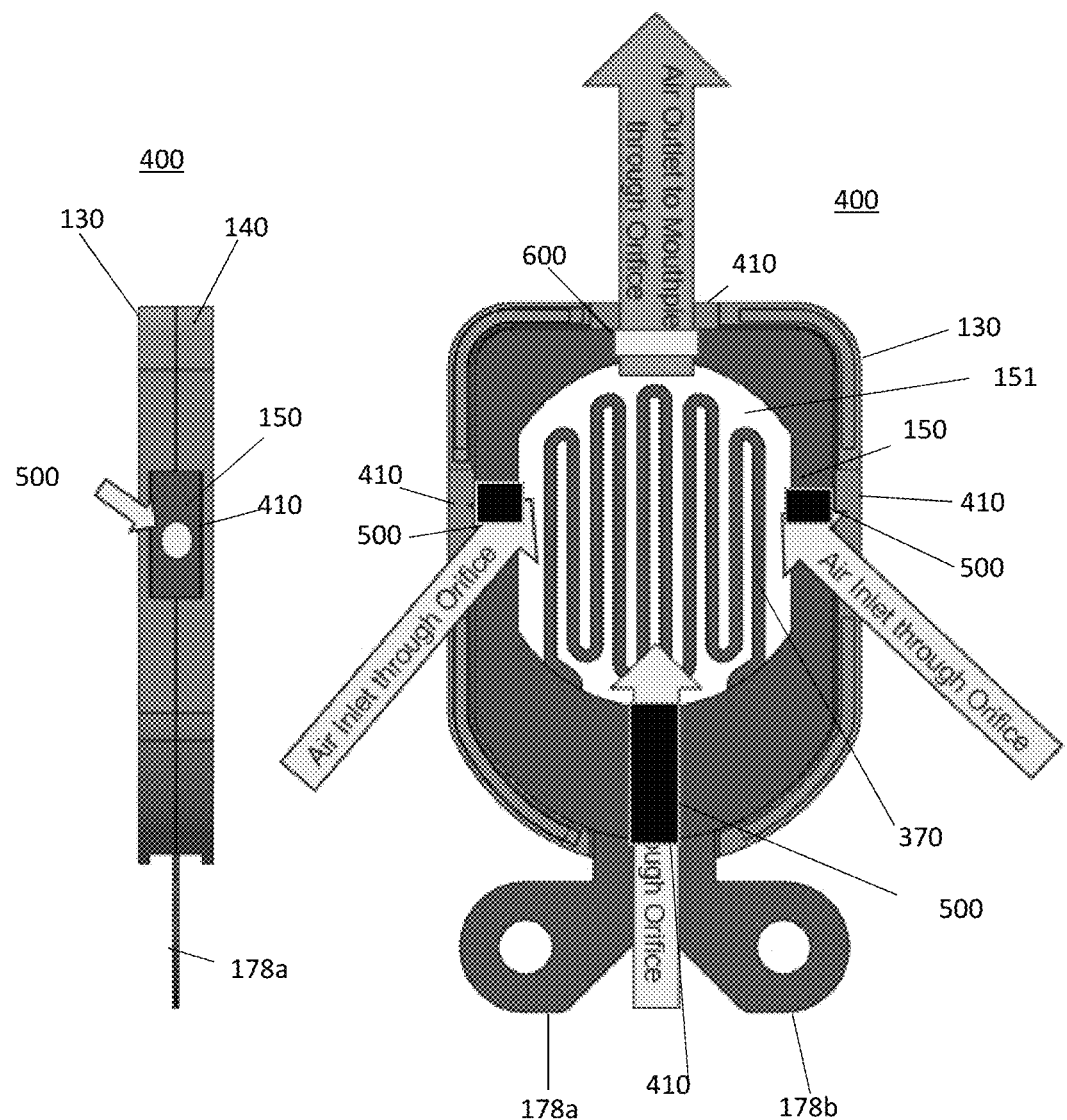

FIG. 18
FIG. 19
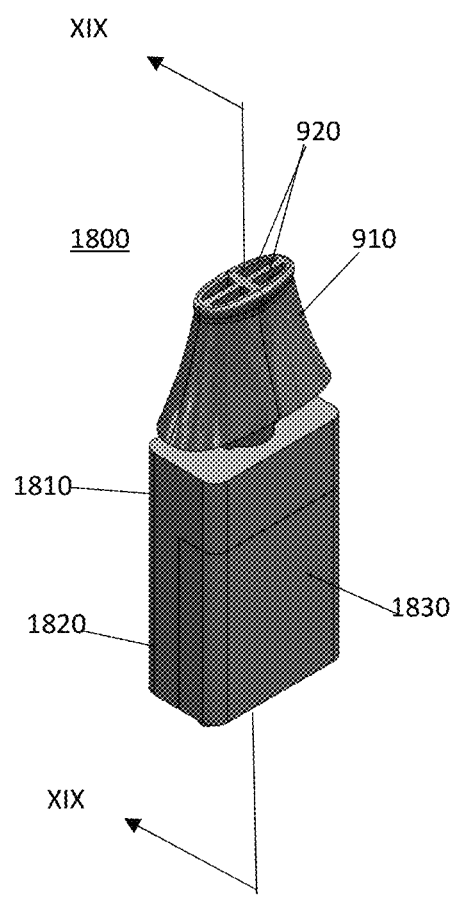
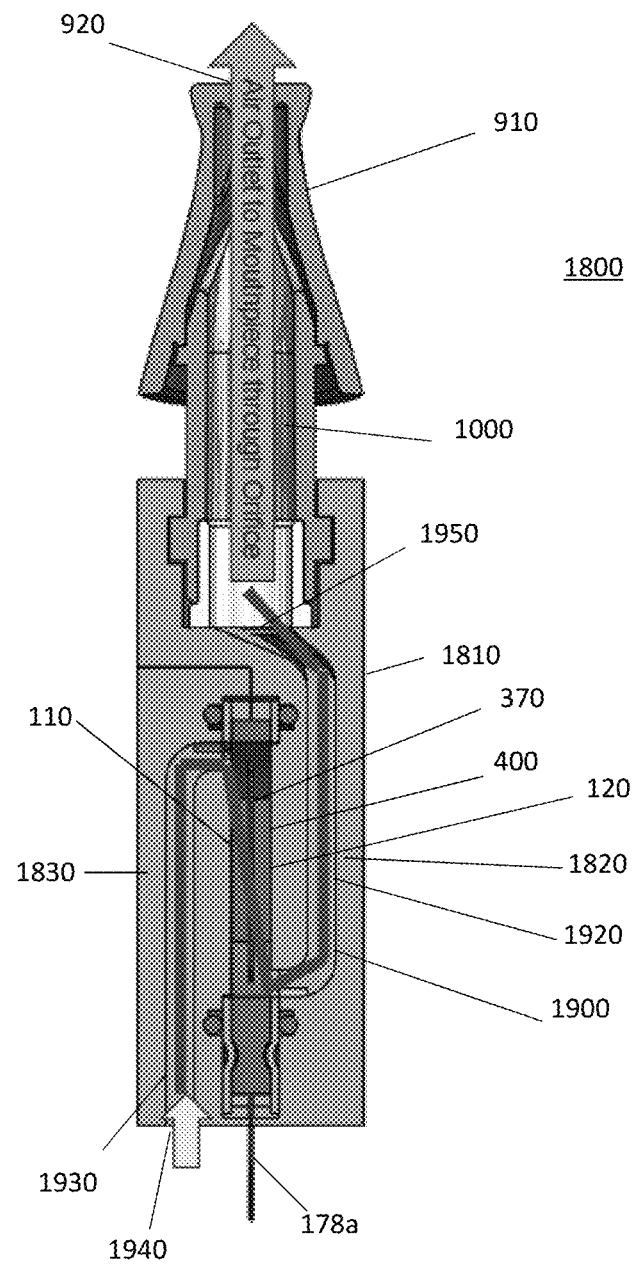

CLOSED SYSTEM CAPSULE WITH AIRFLOW, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one example embodiment relates to a capsule for an aerosol-generating device.

In at least one example embodiment, a capsule for an aerosol-generating device, comprises a housing. The housing includes a first frame defining a cavity. The housing defines at least one air inlet and at least one air outlet. The capsule also includes an aerosol-forming substrate at least partially within the cavity, and a heater supported by the first frame. The heater extends across at least a portion of the cavity. The at least one air inlet, the cavity, and the at least one air outlet collectively form at least one airflow pathway through the capsule. The airflow pathway is longer than a thickness of the capsule.

In at least one example embodiment, the aerosol-forming substrate includes a plant material. The plant material includes tobacco.

In at least one example embodiment, the first frame is an inner frame, and the inner frame comprises a first face, a second face, a first end, a second end, a first side, and a second side. The at least one air inlet extends through the first end of the inner frame and the at least one air outlet extends through the second end of the inner frame. The at least one air inlet includes a first air inlet and a second air inlet. The first air inlet extends through the first side and the second air inlet extends through the first end of the inner frame. The at least one air outlet extends through the second end of the inner frame.

In at least one example embodiment, the capsule further comprises a diffuser configured to redistribute air from the at least one air inlet towards the at least one air outlet. The diffuser includes at least one channel on the first face of the inner frame. The diffuser comprises a main channel extending longitudinally from the at least one air inlet, and at least one secondary channel in fluid communication with the main channel. The at least one secondary channel includes at least one parallel channel extending parallel to the main channel and at least one angled channel extending at an angle with respect to the main channel.

In at least one example embodiment, the heater is sinuously shaped.

At least one example embodiment relates to a capsule assembly for an aerosol-generating device.

In at least one example embodiment, a capsule assembly for an aerosol-generating device comprises a capsule. The capsule includes a housing including a first frame defining a cavity. The capsule also includes an aerosol-forming substrate at least partially within the cavity, and a heater supported by the inner frame. The heater extends across at least a portion of the cavity. The capsule assembly also comprises a capsule enclosure surrounding at least a portion of the housing. The capsule enclosure defines at least one air inlet and the at least air outlet. The at least one air inlet, the cavity, and the at least one air outlet collectively form at least one airflow pathway through the capsule assembly. The airflow pathway is longer than a thickness of the capsule.

In at least one example embodiment, the capsule enclosure further comprises a capsule enclosure airflow channel extending between the at least one air inlet and the at least one air outlet. The capsule enclosure airflow channel defines a portion of the at least one airflow pathway. The at least one airflow pathway extends diagonally across at least a portion of the cavity in the first frame. In at least one example embodiment, the at least one airflow pathway extends diagonally across at least a portion of the heater and the aerosol-forming substrate.

At least one example embodiment relates to an aerosol-generating device.

In at least one example embodiment, an aerosol-generating device comprises a device body configured to receive a capsule. The capsule includes a housing including a first frame defining a cavity, at least one air inlet, and at least one air outlet. The capsule also includes an aerosol-forming substrate at least partially within the cavity, and a heater supported by the first frame and extending across at least a portion of the cavity. The at least one air inlet, the cavity, and the at least one air outlet collectively form at least one airflow pathway through the capsule. The airflow pathway is longer than a thickness of the capsule. The aerosol-generating device also includes a plurality of electrodes within the device body. The plurality of electrodes are configured to electrically contact the heater of the capsule. The aerosol-generating device also includes a power source configured to supply an electric current to the heater of the capsule via the plurality of electrodes.

In at least one example embodiment, the aerosol-forming substrate includes a plant material. The plant material includes tobacco.

In at least one example embodiment, the first frame is an inner frame. The inner frame comprises a first face, a second face, a first end, a second end, a first side, and a second side.

In at least one example embodiment, the at least one air inlet extends through the first end of the inner frame and the at least one air outlet extends through the second end of the inner frame. The at least one air inlet includes a first air inlet and a second air inlet. The first air inlet extends through the first side, the second air inlet extends through the first end of the inner frame, and the at least one air outlet extends through the second end of the inner frame.

In at least one example embodiment, the capsule further comprises a diffuser configured to redistribute air from the at least one air inlet towards the at least one air outlet. The diffuser includes at least one channel on the first face of the inner frame. In at least one example embodiment, the diffuser comprises a main channel extending longitudinally from the at least one air inlet, and at least one secondary channel in fluid communication with the main channel. The at least one secondary channel includes at least one parallel channel extending parallel to the main channel and at least one angled channel extending at an angle with respect to the main channel.

At least one example embodiment relates to a method of generating an aerosol.

In at least one example embodiment, a method of generating an aerosol comprises electrically contacting a plurality of electrodes with a capsule. The capsule includes a housing including an inner frame. The housing defines a cavity, at least one air inlet, and at least one air outlet. An aerosol-forming substrate is at least partially within the cavity. The capsule also includes a heater supported by the inner frame. The heater extends across at least a portion of the cavity. The at least one air outlet, the at least one air inlet, the cavity, and the at least one air outlet collectively form at least one airflow pathway through the capsule. The airflow pathway is longer than a thickness of the capsule. The method also includes supplying an electric current to the heater of the capsule via the plurality of electrodes.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1A is a perspective view of a first side of a capsule for an aerosol-generating device according to an example embodiment.

FIG. 1B is a perspective view of a second side of a capsule for an aerosol-generating device according to an example embodiment.

FIG. 2A is an exploded view of the capsule of FIGS. 1A and 1B according to at least one example embodiment.

FIG. 2B is an exploded view of the capsule of FIGS. 1A and 1B according to at least one example embodiment.

FIG. 3 is a plan view of a patterned sheet in connection with the fabrication of a heater according to at least one example embodiment.

FIG. 4 is a view of a capsule including the heater of FIG. 3 with the second frame removed according to at least one example embodiment.

FIG. 5 is a side view of the capsule of FIG. 4 according to at least one example embodiment, a fourth side being a mirror image of the third side.

FIG. 6 is a view of the capsule of FIG. 5 with the second frame removed illustrating airflow therethrough according to at least one example embodiment.

FIG. 7 is a view the capsule of FIG. 4 illustrating an alternative airflow path therethrough according to at least one example embodiment.

FIG. 8 is a view the capsule of FIG. 4 illustrating an alternative airflow path therethrough according to at least one example embodiment.

FIG. 9 is a perspective view of a capsule assembly including a capsule connected with a mouthpiece according to at least one example embodiment.

FIG. 10 is a side cross-sectional view of the capsule assembly of FIG. 9 according to at least one example embodiment.

FIG. 11 is a side cross-sectional view along line XI-XI of the capsule assembly of FIG. 10 according to at least one example embodiment.

FIG. 12 is a side cross-sectional view of the assembly of FIG. 9 according to at least one example embodiment.

FIG. 13 is a side cross-sectional view along line XIII-XIII of the capsule assembly of FIG. 12 according to at least one example embodiment.

FIG. 14 is a side cross-sectional view of the capsule assembly of FIG. 9 according to at least one example embodiment.

FIG. 15 is a side cross-sectional view along line XV-XV of the capsule assembly of FIG. 14 according to at least one example embodiment.

FIG. 16 is a side cross-sectional view of the capsule assembly of FIG. 9 according to at least one example embodiment.

FIG. 17 is a side cross-sectional view along line XVII-XVII of the capsule assembly of FIG. 16 according to at least one example embodiment.

FIG. 18 is a side perspective view of a capsule assembly including a capsule enclosed in a capsule enclosure and connected to a mouthpiece according to at least one example embodiment.

FIG. 19 is a side cross-sectional view along line XIX-XIX of the capsule, assembly of FIG. 18 according to at least one example embodiment.

FIG. 20 is a side cross-sectional view of the capsule assembly of FIG. 18 according to at least one example embodiment.

FIG. 21 is a side cross-sectional view of the capsule assembly of FIG. 18 according to at least one example embodiment.

FIG. 22 is a side cross-sectional view of the capsule assembly of FIG. 18 according to at least one example embodiment.

FIG. 23 is a schematic illustration of an aerosol generating device for use with a capsule or capsule assembly according to at least one example embodiment.

DETAILED DESCRIPTION

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

The processing circuitry (control circuitry) may be hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Figure 1A:
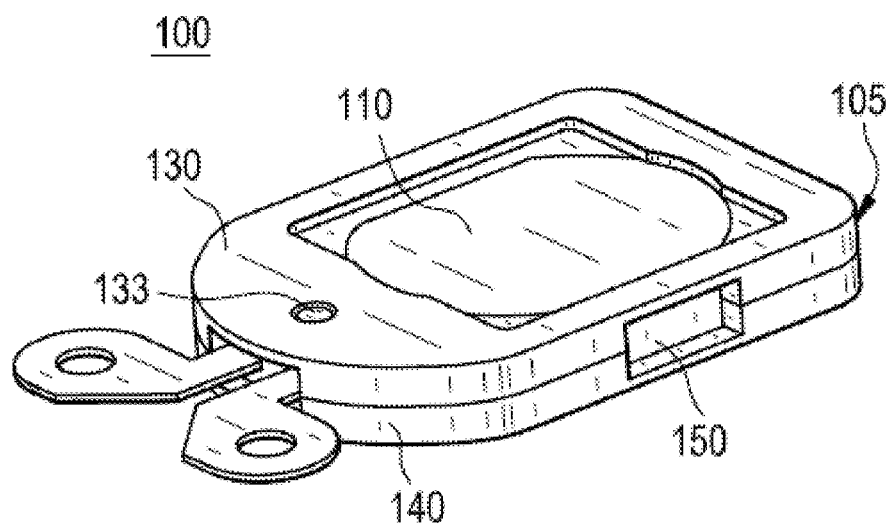
FIG. 1A is a perspective view of a first side of a capsule for an aerosol-generating device according to an example embodiment.

In at least one example embodiment, as shown in FIGS. 1A, 1B, 2A, and 2B, the capsule 100 may be configured to be received within an aerosol-generating device (e.g., heat-not-burn aerosol-generating device). In the drawings, the capsule 100 has a laminar structure and a generally planar form. The proximal end of the capsule 100 may have a curved proximal edge, and the opposing distal end may have a linear distal edge. In addition, a pair of linear side edges may connect the curved proximal edge and the linear distal edge. The pair of linear side edges may be parallel to each other. Furthermore, the junctions of the linear side edges with the linear distal edge may be in the form of rounded corners.

Although the capsule 100 is shown in the figures as resembling a rectangle with a semicircular end (e.g., elongated semicircle, semi-obround), it should be understood that other configurations may be employed. For instance, the shape may be circular such that the capsule 100 has a disk-like appearance. In another instance, the shape of the capsule 100 may be elliptical or racetrack-like. In other instances, the capsule 100 may have a polygonal shape (regular or irregular), including a triangle, a rectangle (e.g., square), a pentagon, a hexagon, a heptagon, or an octagon. The laminar structure and generally planar form of the capsule 100 may facilitate stacking so as to allow a plurality of capsules to be stored in an aerosol-generating device or other receptacle for dispensing a new capsule or receiving a depleted capsule. In an example embodiment, the capsule 100 has a thickness between 1-4 mm (e.g., between 1-2 mm).

The capsule 100 may include a housing 105 and a heater 170 within the housing 105. The housing 105 of the capsule 100 has interior surfaces defining a chamber configured to hold an aerosol-forming substrate 160 (e.g., FIGS. 2A and 2B). In addition, the housing of the capsule 100 has exterior surfaces constituting a first face, an opposing second face, and a side face of the capsule 100. The first face and the second face of the capsule 100 may be permeable or impermeable to an aerosol based on a desired airflow path through the capsule and/or along and across the heater. The side face of the capsule 100 is between the first face and the second face. The side face may be regarded as a periphery of the capsule 100.

The housing of the capsule 100 includes a first frame 130 and a second frame 140. The first frame 130 and the second frame 140 may be of the same shape and size (e.g., based on a plan view) and aligned such that the outer sidewalls are substantially flush with each other, although example embodiments are not limited thereto. The first frame 130 and the second frame 140 may be formed of a suitable polymer, such as polyether ether ketone (PEEK), liquid crystal polymer (LCP), and/or ultra-high molecular weight polyethylene (UHMWPE). The first frame 130 and the second frame 140 may be connected via a welded arrangement.

A first permeable or impermeable structure 110 is secured and exposed by the first frame 130. Similarly, a second permeable or impermeable structure 120 is secured and exposed by the second frame 140. As will be discussed in more detail herein, a third frame (or inner frame) 150 is disposed between the first permeable or impermeable structure 110 and the second permeable or impermeable structure 120 (as well as between the first frame 130 and the second frame 140). The capsule 100 is configured to hold an aerosol-forming substrate 160 (shown and described with respect to FIGS. 2A and 2B), which may be within the third frame 150 and between the first permeable or impermeable structure 110 and the second permeable or impermeable structure 120. A first concavity 133 (e.g., first dimpled portion) in the first frame 130 and a second concavity 143 (e.g., second dimpled portion) in the second frame 140 may be from an injection molding process. In this regard, the size, location, and/or shape of the first concavity 133 and the second concavity 143 may differ (or may be absent altogether) depending on the fabrication technique.

The first permeable or impermeable structure 110 and the second permeable or impermeable structure 120 may be in a form of a mesh sheet, a perforated sheet, a solid sheet, or any combination thereof. For instance, both the first permeable or impermeable structure 110 and the second permeable or impermeable structure 120 may be in a form of a solid sheet so as to form a substantially sealed capsule structure if desired to ensure airflow along the aerosol-forming substrate 160 and/or the heater 170. In another instance, both the first permeable or impermeable structure 110 and the second permeable or impermeable structure 120 may be in a form of a perforated sheet (e.g., 80, 100, or 250 mesh equivalent) so as to allow airflow into the capsule. The perforated sheet may be one that is perforated mechanically or chemically (e.g., via photochemical machining/etching). In yet another instance, one of the first permeable or impermeable structure 110 or the second permeable or impermeable structure 120 may be in a form of a mesh sheet, while the other of the first permeable or impermeable structure 110 or the second permeable or impermeable structure 120 may be in a form of a perforated sheet. The first permeable or impermeable structure 110 and the second permeable or impermeable structure 120 (as well as the first frame 130 and the second frame 140) may be substantially the same size based on a plan view (e.g., ±10% of a given dimension).

Figure 1B:
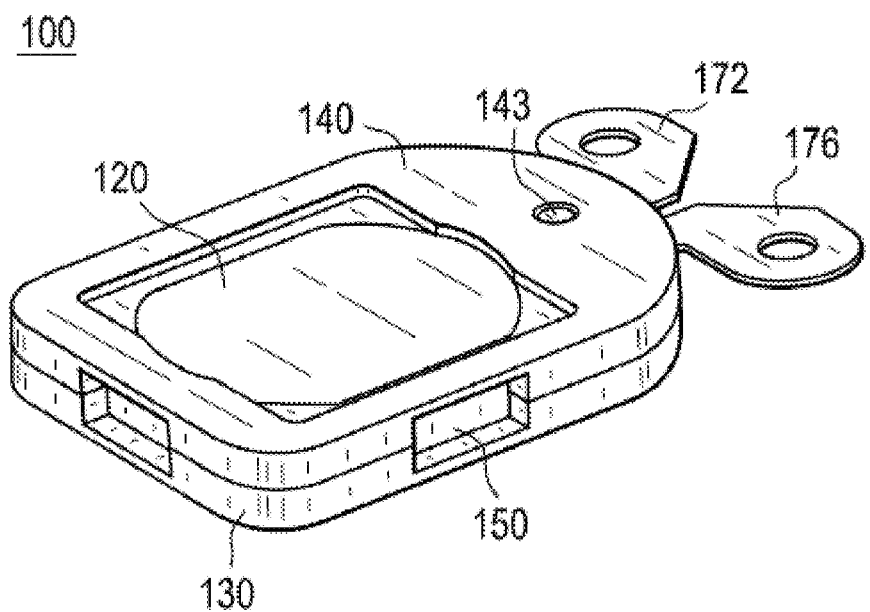
FIG. 1B is a perspective view of a second side of a capsule for an aerosol-generating device according to an example embodiment.

As shown in FIG. 1A, the combination of the exposed surface of the first permeable or impermeable structure 110 and the adjacent (e.g., substantially coplanar/parallel) surface of the first frame 130 may be regarded as the first face of the capsule 100. Similarly, as shown in FIG. 1B, the combination of the exposed surface of the second permeable or impermeable structure 120 and the adjacent (e.g., substantially coplanar/parallel) surface of the second frame 140 may be regarded as the second face of the capsule 100. In at least one example embodiment, the first face, the second face, or both may include perforated sheets. In at least one example embodiment, the first face, the second face, or both may include mesh sheets. In yet another example embodiment, one of the first face or the second face may include a perforated sheet, while the other of the first face or the second face may include a mesh sheet. In at least one example embodiment, the first face, the second face, or both may include solid sheets so as to substantially seal the capsule except for air inlets and outlets as described herein with respect to FIGS. 4-23.

As noted supra and as will be discussed herein in more detail, a heater 170 (e.g., FIGS. 2A, 2B, and 3) may be disposed within the capsule 100 to heat the aerosol-forming substrate 160. The heater 170 may include, inter alia, a first end section 172 and a second end section 176 configured to receive an electric current from a power source during an activation of the heater 170. When the heater 170 is activated, the temperature of the aerosol-forming substrate 160 may increase, and an aerosol may be generated and released from the capsule 100.

As shown in FIGS. 1A-1B, the combination of the exposed surfaces of the third frame 150 and the adjacent sidewalls of the first frame 130 and the second frame 140 may be regarded as the side face of the capsule 100. Additionally, the first end section 172 and the second end section 176 may be external segments of the heater 170 that also constitute parts of the side face of the capsule 100. The outward-facing surfaces of the first end section 172 and the second end section 176 of the heater 170 may be coplanar, although example embodiments are not limited thereto.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater (e.g., heater 170 shown in FIGS. 2A and 2B) may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include a synthetic material. In another instance, the fibrous material may include a natural material such as a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

Figure 2A:
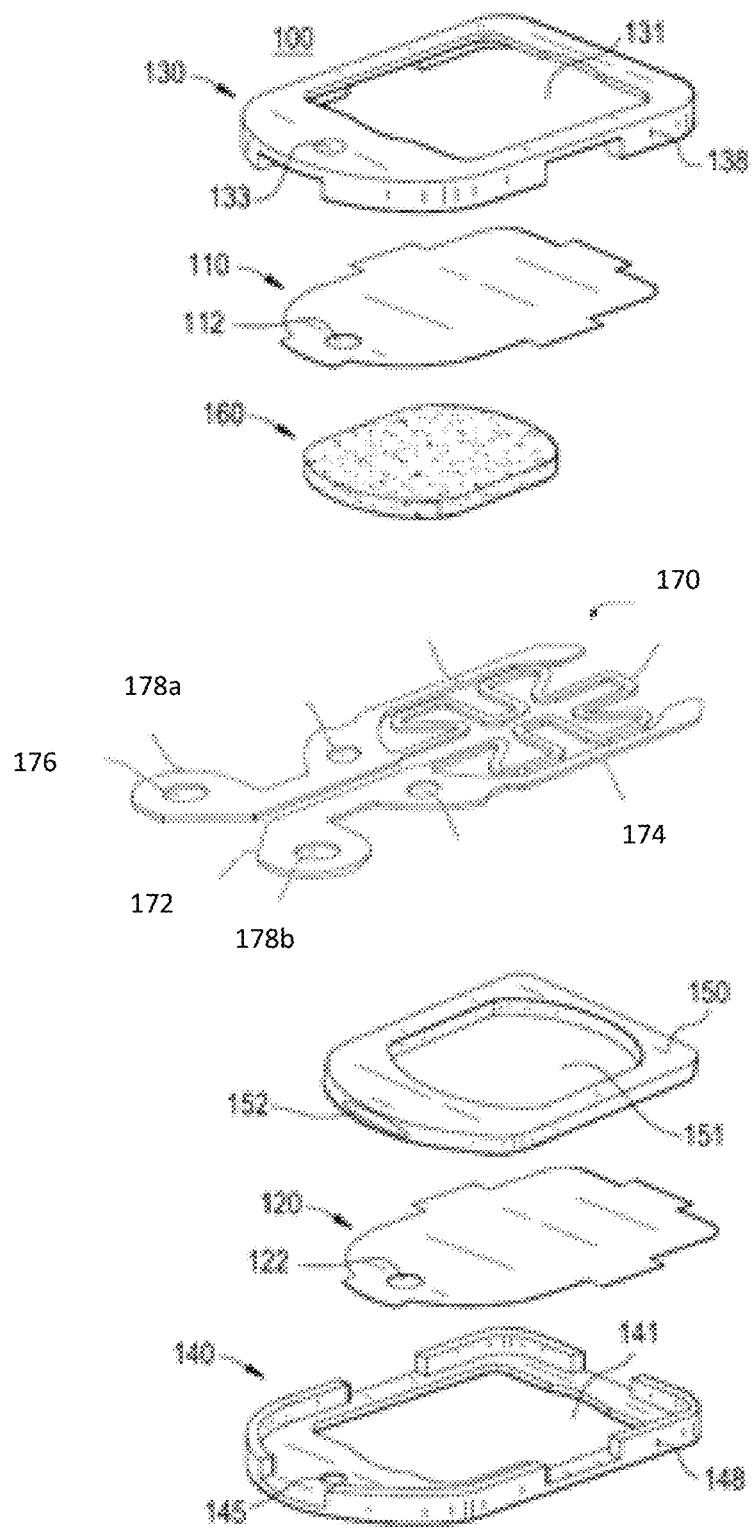
FIG. 2A is an exploded view of the capsule of FIGS. 1A and 1B according to at least one example embodiment.
Figure 2B:
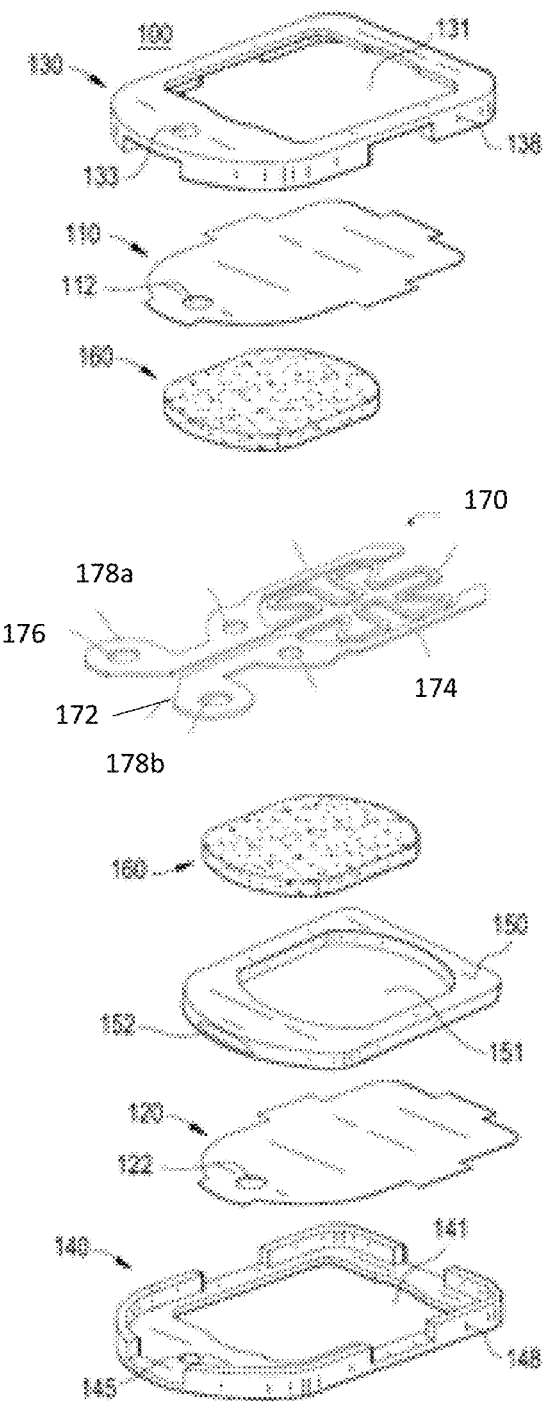
FIG. 2B is an exploded view of the capsule of FIGS. 1A and 1B according to at least one example embodiment.

Referring to FIGS. 2A and 2B, the first frame 130 has a first interior face and a first exterior face. In addition, the first frame 130 defines a first opening 131. In an example embodiment, the sidewall of the first opening 131 has opposing linear sections and, optionally, opposing curved sections, wherein one curved section may be adjacent to the proximal end of the first frame 130, and the other curved section may be adjacent to the opposing distal end of the first frame 130. The first permeable or impermeable structure 110 may be secured to the first interior face of the first frame 130 so as to be exposed by the first opening 131. From a difference perspective, the first permeable or impermeable structure 110 may also be regarded as covering the first opening 131. Furthermore, the first permeable or impermeable structure 110 may define a first aperture 112. The first aperture 112 may be positioned and sized so as to accommodate the first convexity (not shown), which corresponds to first concavity 133 shown in FIGS. 2A and 2B, when the first permeable or impermeable structure 110 is secured to the first frame 130.

The second frame 140 has a second interior face and a second exterior face. In addition, the second frame 140 defines a second opening 141. In an example embodiment, the sidewall of the second opening 141 has opposing linear sections and, optionally, opposing curved sections, wherein one curved section may be adjacent to the proximal end of the second frame 140, and the other curved section may be adjacent to the opposing distal end of the second frame 140. The second permeable or impermeable structure 120 may be secured to the second interior face of the second frame 140 so as to be exposed by the second opening 141. From a different perspective, the second permeable or impermeable structure 120 may also be regarded as covering the second opening 141. The size and shape of the second opening 141 may correspond to (e.g., mirror) the size and shape of the first opening 131. Furthermore, the second permeable or impermeable structure 120 may define a second aperture 122. The second aperture 122 may be positioned and sized so as to accommodate the second convexity 145 when the second permeable or impermeable structure 120 is secured to the second frame 140.

The third frame 150 defines a cavity 151 configured to receive the aerosol-forming substrate 160. The combination of the sidewall of the cavity 151 and the interior surfaces of the first permeable or impermeable structure 110 and the second permeable or impermeable structure 120 (which cover the cavity 151) may be regarded as defining a chamber. In an example embodiment, the sidewall of the cavity 151 has opposing linear sections and opposing curved sections, wherein one curved section is adjacent to the proximal end of the third frame 150, and the other curved section is adjacent to the opposing distal end of the third frame 150. The third frame 150 may be substantially the same size as the first permeable or impermeable structure 110 and the second permeable or impermeable structure 120 based on a plan view (e.g., ±10% of a given dimension). The third frame 150 may also define at least one aperture 152 adjacent to an end of the third frame 150. In addition to the materials of construction for the first frame 130 and the second frame 140, the third frame 150 may also be formed of other suitable materials, such as ceramic, sintered glass, and/or consolidated fibers (e.g., cardboard).

In at least one example embodiment, a heater 170 is configured to extend through the third frame 150 and into the cavity 151. Additionally, the heater 170 may be regarded as being supported by the third frame 150. The heater 170 includes a first end section 172, an intermediate section 174, and a second end section 176. The first end section 172 and the second end section 176 of the heater 170 are external segments that also constitute parts of the side face of the capsule 100. The intermediate section 174 of the heater 170 is an internal segment disposed within the capsule 100 (e.g., within the chamber of the housing containing the aerosol-forming substrate 160). The first end section 172, the intermediate section 174, and the second end section 176 of the heater 170 are sections of a continuous structure. In an example embodiment, the intermediate section 174 of the heater 170 has a planar and winding form.

When the heater 170 is activated, the temperature of the aerosol-forming substrate may increase, and an aerosol may be generated and released from the capsule 100.

In at least one example embodiment, the heater 170 may be formed from a sheet material that may be cut, photo-etched, and stamped into a corrugated form or otherwise processed (e.g., electrochemical etching, die cutting, laser cutting).

In an example embodiment, the heater 170 is configured to undergo Joule heating (which is also known as ohmic/resistive heating) upon the application of an electric current thereto. Stated in more detail, the heater 170 may be formed of one or more conductors and configured to produce heat when an electric current passes therethrough. The electric current may be supplied between the first end section 172 and the second end section 176 of the heater 170 from a power source (e.g., battery) within the aerosol-generating device. Suitable conductors for the heater 170 include an iron-based alloy (e.g., stainless steel, iron aluminides), a nickel-based alloy (e.g., nichrome), and/or a ceramic (e.g., ceramic coated with metal). The intermediate section 174 of the heater 170 may have a thickness of about 0.1-0.3 mm (e.g., 0.15-0.25 mm) and a resistance of about 0.5-2.5 Ohms (e.g., 1-2 Ohms).

The electric current from the power source within the aerosol-generating device may be transmitted via electrodes configured to electrically contact the first end section 172 and the second end section 176 of the heater 170 when the capsule 100 is inserted into the aerosol-generating device. In a non-limiting embodiment, the electrodes within the aerosol-generating device may be spring-loaded to enhance an engagement with the heater 170 of the capsule 100. For instance, a spring-loaded first electrode within the aerosol-generating device may have a rounded or beveled engagement portion configured to electrically contact the first end section 172 of the heater 170 such that the engagement portion is seated within the aperture in the first end section 172. Similarly, a spring-loaded second electrode within the aerosol-generating device may have a rounded or beveled engagement portion configured to electrically contact the second end section 176 of the heater 170 such that the engagement portion is seated within the aperture in the second end section 176. In such instances, the engagement of the first electrode and the second electrode of the aerosol-generating device with the first end section 172 and the second end section 176, respectively, of the heater 170 may produce a confirmatory click. The spring-loading of the electrodes may be in a direction that is orthogonal to the plane of the heater 170. In addition to or in lieu of the spring-loading, the movement (e.g., engagement, release) of the electrodes may be achieved by mechanical actuation. Furthermore, the supply of the electric current from the aerosol-generating device to the capsule 100 may be a manual operation (e.g., button-activated) or an automatic operation (e.g., puff-activated).

The aerosol-forming substrate 160 may be disposed within the cavity 151 of the third frame 150 so as to be on one side (as shown in FIG. 2A) or both sides (as shown in FIG. 2B) of the intermediate section 174 of the heater 170. In at least one example embodiment, the aerosol-forming substrate 160 may be in a consolidated form (e.g., sheet, pallet, tablet) that is configured to maintain its shape so as to allow the aerosol-forming substrate 160 to be placed in a unified manner within the cavity 151 of the third frame 150. In such an instance, one mass of the aerosol-forming substrate 160 may be disposed on one side of the intermediate section 174 of the heater 170 as shown in FIG. 2A. In another example embodiment, as shown in FIG. 2B, one mass of the aerosol-forming substrate 160 may be disposed on one side of the intermediate section 174 of the heater 170, while another mass of the aerosol-forming substrate 160 may be disposed on the other side of the intermediate section 174 of the heater 170 (e.g., so as to substantially fill the cavity 151 of the third frame 150 and sandwich/embed the intermediate section 174 of the heater 170 in between). Alternatively, the aerosol-forming substrate 160 may be in a loose form (e.g., particles, fibers, grounds, fragments, shreds) that does not have a set shape but rather is configured to take on the shape of the cavity 151 of the third frame 150 when introduced.

The first permeable or impermeable structure 110 and the second permeable or impermeable structure 120 may be secured to the first frame 130 and the second frame 140, respectively, via a variety of attachment techniques. For instance, the attachment technique may involve injection molding (e.g., insert molding, over molding). In another instance, the attachment technique may involve ultrasonic welding. In other instances, the attachment technique may involve an adhesive (e.g., tape, glue) that has been deemed food-safe or otherwise acceptable by a regulatory authority. Alternatively, in lieu of a separate attachment technique, the first permeable or impermeable structure 110 and the second permeable or impermeable structure 120 may be clamped against the third frame 150 (or otherwise constrained) by the first frame 130 and the second frame 140, respectively.

As shown in FIGS. 2A and 2B, the first frame 130 includes at least one first connector protruding from the first interior face of the first frame 130. The at least one first connector of the first frame 130 may be in a form of a first connector 138. In an example embodiment, the first connector 138 may extend along an edge of the first interior face of the first frame 130 in a form a ridge (e.g., first ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the first connector 138 is shown as being separated into a plurality of discrete structures (e.g., four discrete structures), it should be understood that example embodiments are not limited thereto. For instance, alternatively, the first connector 138 may be a single, continuous structure extending along the edge so as to completely surround the first interior face of the first frame 130.

Similarly, the second frame 140 includes at least one second connector protruding from the second interior face of the second frame 140. The at least one second connector of the second frame 140 may be in a form of a second connector 148. The second connector 148 of the second frame 140 and the first connector 138 of the first frame 130 are complementary structures configured to mate with each other. In an example embodiment, the second connector 148 may extend along an edge of the second interior face of the second frame 140 in a form a ridge (e.g., second ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the second connector 148 is shown as being separated into a plurality of discrete structures (e.g., four discrete structures), it should be understood that example embodiments are not limited thereto. For instance, alternatively, the second connector 148 may be a single, continuous structure extending along the periphery so as to completely surround the second interior face of the second frame 140.

In the non-limiting embodiment illustrated in FIGS. 2A and 2B where the first connector 138 of the first frame 130 is separated into four discrete structures, two of the structures may be elevated trenches, while the other two structures may be tapered ridges. Conversely, the second connector 148 of the second frame 140 may be separated into four discrete structures, wherein two of the structures are tapered ridges, while the other two structures are elevated trenches. The mixed set of elevated trenches and tapered ridges of the first frame 130 are configured to mate with the mixed set of tapered ridges and elevated trenches, respectively, of the second frame 140 during the assembly of the capsule 100. It should be understood that various combinations of elevated trenches and the tapered ridges are possible for the first frame 130 and the second frame 140. Furthermore, each of the first permeable or impermeable structure 110 and the second permeable or impermeable structure 120 may have tab-like extensions (e.g., four tab-like extensions) disposed between the discrete structures of the first connector 138 and the second connector 148, respectively, when the capsule 100 is assembled.

A tapered ridge of the first connector 138 and/or the second connector 148 may have a shoulder portion and an inclined portion that rises from the shoulder portion to form a tapered ridgeline. The tapered ridgeline may function as an energy director during assembly (e.g., to facilitate welding). A corresponding elevated trench of the first connector 138 and/or the second connector 148 may have a rim portion and a trench bottom. As shown in FIGS. 2A and 2B, the trench bottom of the elevated trench may be a planar bottom. Alternatively, the trench bottom of the elevated trench may be a V-shaped bottom. In an example embodiment of a connection between the first frame 130 and the second frame 140, the inclined portion of a tapered ridge is configured to contact the trench bottom of a corresponding elevated trench, while the shoulder portion of the tapered ridge interfaces with the rim portion of the elevated trench. Thus, the engagement surfaces of the first connector 138 and the second connector 148 may be inversely or complementarily configured to facilitate mating.

When the mixed set of elevated trenches and tapered ridges of each frame are grouped such that the elevated trenches are on one linear side edge while the tapered ridges are on the other linear side edge, as shown in FIGS. 2A and 2B, the first frame 130 and the second frame 140 may be identical parts. In such an instance, orienting the first frame 130 and the second frame 140 to face each other for mating will result in a complementary arrangement. As a result, one part may be used interchangeably as the first frame 130 or the second frame 140, thus simplifying the method of manufacturing.

To assemble the capsule 100, the first frame 130 may be connected to the second frame 140 after an aerosol-forming substrate 160 is disposed within the cavity 151 of the third frame 150 (e.g., so as to be on both sides of the intermediate section 174 of the heater 170). In such an instance, the third frame 150 will be sandwiched between the first permeable or impermeable structure 110 and the second permeable or impermeable structure 120 when the first frame 130 is connected to the second frame 140. During assembly, the at least one first connector of the first frame 130 is configured to engage with the at least one second connector of the second frame 140 to form at least one connection (e.g., four connections). For instance, an elevated trench (and/or tapered ridge) of the first connector 138 is configured to mate with a corresponding tapered ridge (and/or elevated trench) of the second connector 148. In addition, the joinder between the first connector 138 of the first frame 130 and the second connector 148 of the second frame 140 may be achieved via a welded arrangement (e.g., ultrasonic welding). Furthermore, the outer sidewall of the first frame 130 may be substantially flush with the outer sidewall of the second frame 140 when the capsule 100 is assembled, although example embodiments are not limited thereto. Once assembled, the capsule 100 is difficult or impracticable to open without damaging the connectors, the frames, and/or other aspects of the capsule 100. As a result, the capsule 100 is relatively tamper-proof against unauthorized actions by third parties.

The capsule 100 has been described as including, inter alia, a first frame 130 that is separate from a second frame 140. Alternatively, in some instances, the first frame 130 and the second frame 140 may be fabricated as a single structure that is configured to fold during assembly such that the first connector 138 engages with the second connector 148. For example, the first frame 130 and the second frame 140 may resemble a clamshell structure, wherein the linear distal edge of the first frame 130 is connected to the linear distal edge of the second frame 140 with an integral section of reduced thickness that functions as a fold line. In another example, a linear side edge of the first frame 130 may be connected to a linear side edge of the second frame 140 with an integral section of reduced thickness that functions as a fold line. With a clamshell structure, it should be understood that one or more connections (e.g., along the fold line) may be omitted from the capsule 100.

Figure 3:
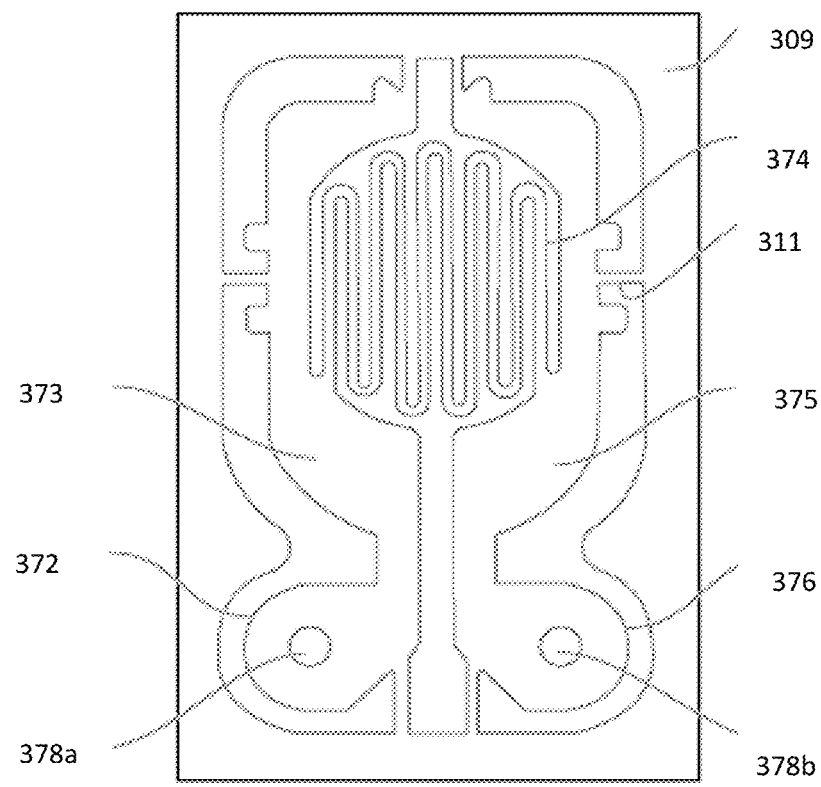

FIG. 3 is a plan view of a patterned sheet in connection with the fabrication of a heater according to at least one example embodiment.

In at least one example embodiment, as shown in FIG. 3, a sheet material may be cut or otherwise processed (e.g., stamping, electrochemical etching, die cutting, laser cutting) to produce a patterned sheet 370. As shown, the patterned sheet 370 includes a heater having a first end section 372, a first arm portion 373, an intermediate section 374, a second arm portion 375, and a second end section 376. The first end section 372 and the second end section 376 may define apertures 378a and 378b, respectively. The first arm portion 373 and the second arm portion 375 may function as support structures as well as thermal relief segments. The intermediate section 374 may have a winding form resembling a compressed oscillation or zigzag with a plurality of parallel segments (e.g., eight to twelve parallel segments). The parallel segments can be connected via U-shaped end portions as shown in FIG. 3. A sheet portion 309 is connected to the first end section 372, the first arm portion 373, the second arm portion 375, and the second end section 376 via breakout portions 311. During a subsequent step of the fabrication process, the breakout portions 311 are cut to allow the first end section 372, the first arm portion 373, the second arm portion 375, and the second end section 376 of the heater to be separated from the sheet portion 309. Although six breakout portions 311 are illustrated, it should be understood that example embodiments are not limited thereto. Furthermore, the first arm portion 373 and the second arm portion 375 may include alignment tabs (e.g., six alignment tabs) adjacent to the breakout portions 311 to facilitate a placement of the heater during the assembly of the capsule.

Figure 4:
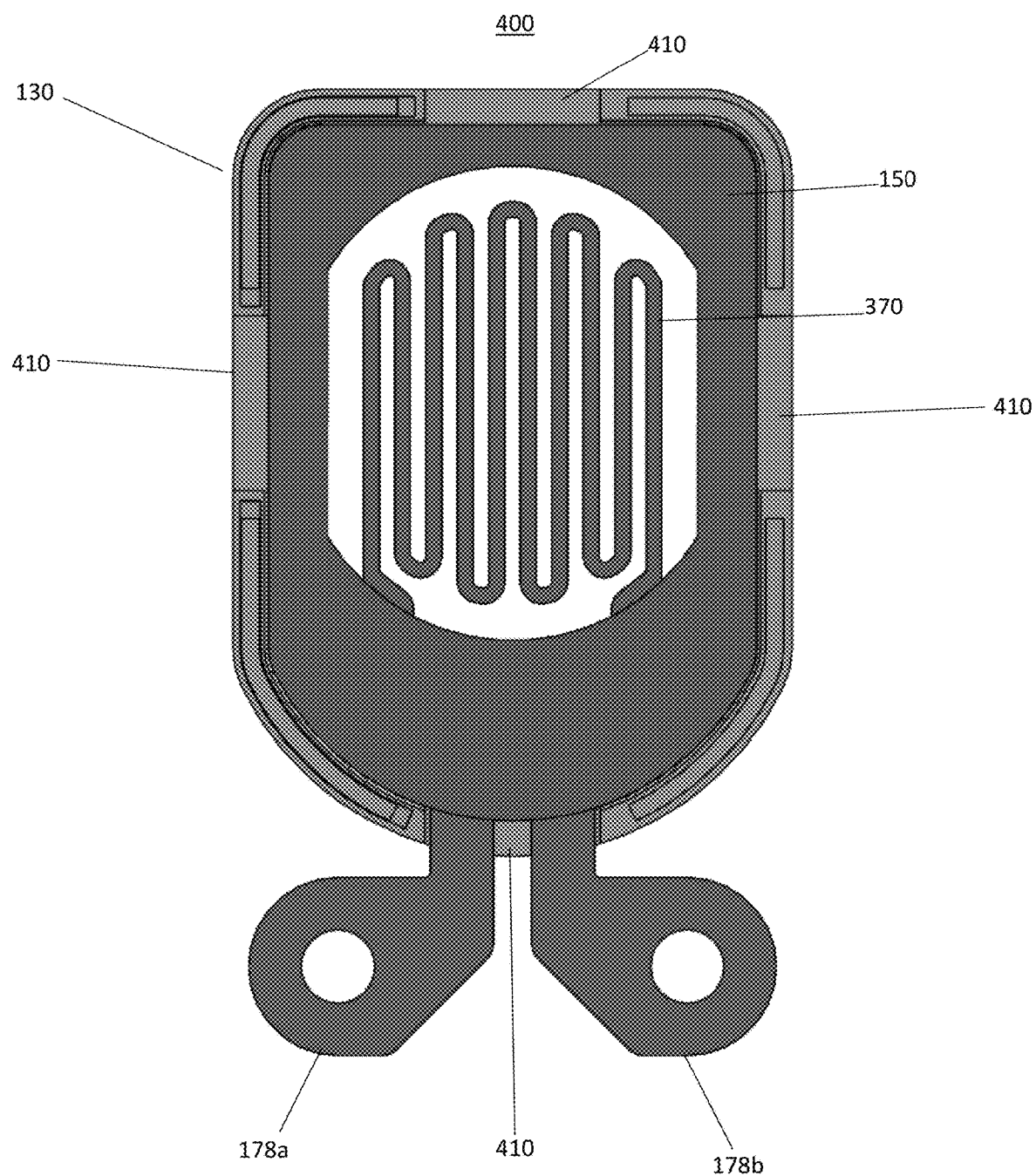

FIG. 4 is a view of a capsule including the heater of FIG. 3 with the second frame removed according to at least one example embodiment.

In an example embodiment, as shown in FIG. 4, the capsule is the same as the capsule of FIGS. 1A, 1B, 2A, and 2B, except that the capsule 400 includes the heater 370 shown and described with respect to FIG. 3 and the second frame 140 has been removed to show the inner frame 150, the heater 370, and openings 410 at least partially defined by the first frame 130. While not shown in FIG. 4, the openings 410 are also at least partially defined by the second frame 140, such that when the first frame 130 is joined with the second frame 140, the openings 410 expose portions of the inner (third) frame 150.

FIG. 5 is a side view of the capsule of FIG. 4 according to at least one example embodiment, a fourth side being a mirror image of the third side.

In at least one example embodiment, as shown in FIG. 5, the capsule 400 of FIG. 4 is shown with the second frame 140 joined with the first frame 130, such that the opening 410 exposes the inner frame 150. An opening 410 is also on the opposite side of the capsule 400, but not shown. As shown, the inner frame 150 defines at least one air passage 500 leading from a side edge of the inner frame 150 to the cavity 151 (shown in FIG. 6). In at least one example embodiment, the at least one air passage 500 aligns with the at least one opening 410 so as to allow airflow through the at least one opening 410, through the at least one air passage 500 to the cavity 151, and across the heater 370.

In at least one example embodiment, a diameter of the at least one air passage 500 ranges from about 0.1 mm to about 5 mm (e.g., about 0.15 mm to about 4.5 mm, about 0.20 mm to about 4.0 mm, or about 1.25 mm to about 3.5 mm). The diameter of the air passages 500 can be altered so as to achieve a desired resistance-to-draw (RTD) of the aerosol-generating device.

In at least one example embodiment, the capsule 400 has a thickness ranging from 1.0 mm to 10.0 mm (e.g. about 2.0 mm to about 9.0 mm, about 3.0 mm to about 8.0 mm, about 4.0 mm to about 7.0 mm or about 5.0 mm to about 6.0 mm).

FIG. 6 is a view of the capsule of FIG. 5 with the second frame removed illustrating airflow therethrough according to at least one example embodiment.

In at least one example embodiment, as shown in FIG. 6, the capsule 400 includes four openings 410 defines between the first frame 130 and the second frame 140 (as shown in FIG. 5). Each of the openings 410 aligns with an air passage 500 or outlet 600 defined in and extending through the inner frame 150. When the capsule 400 is placed in an aerosol-generating device (see FIG. 23) and activated, air is drawn through the openings 410 between tab portions 178a, 178b of the first end section 172 and the second end section 176 and the openings 410 along the sides of the inner frame 150, and through the air passages 500 in the inner frame. After passing through the air passages 500, the air travels across the heater 370 and the aerosol-generating material (shown in FIGS. 2A and 2B) and exits the capsule 400 via the outlet 600. In at least one example embodiment, the air and/or vapor exiting via the outlet 600 may then pass through a mouthpiece (described further with respect to FIGS. 9-23). The capsule 400 is generally sealed so as to promote good airflow through all of the openings 410 and air passages 500 as air is pulled through the outlet 600. For example, the first and second permeable or impermeable structures 110, 120 (shown in FIGS. 1A, 1B, 2A, and 2B) are air impermeable so as to seal the capsule 400 in at least one example embodiment. Since the capsule 400 is sealed, the air flows generally longitudinally across the heater 370 and the aerosol-forming substrate (shown in FIGS. 2A and 2B) so as to prolong contact with the heater 370 and the aerosol-forming substrate.

In at least one example embodiment, a diameter of the outlet 600 ranges from about 0.1 mm to about 5 mm (e.g., about 0.15 mm to about 4.5 mm, about 0.20 mm to about 4.0 mm, or about 0.25 mm to about 3.5 mm). The diameter of the outlet 600 can be altered so as to achieve a desired resistance-to-draw (RTD) of the aerosol-generating device.

Figure 7:
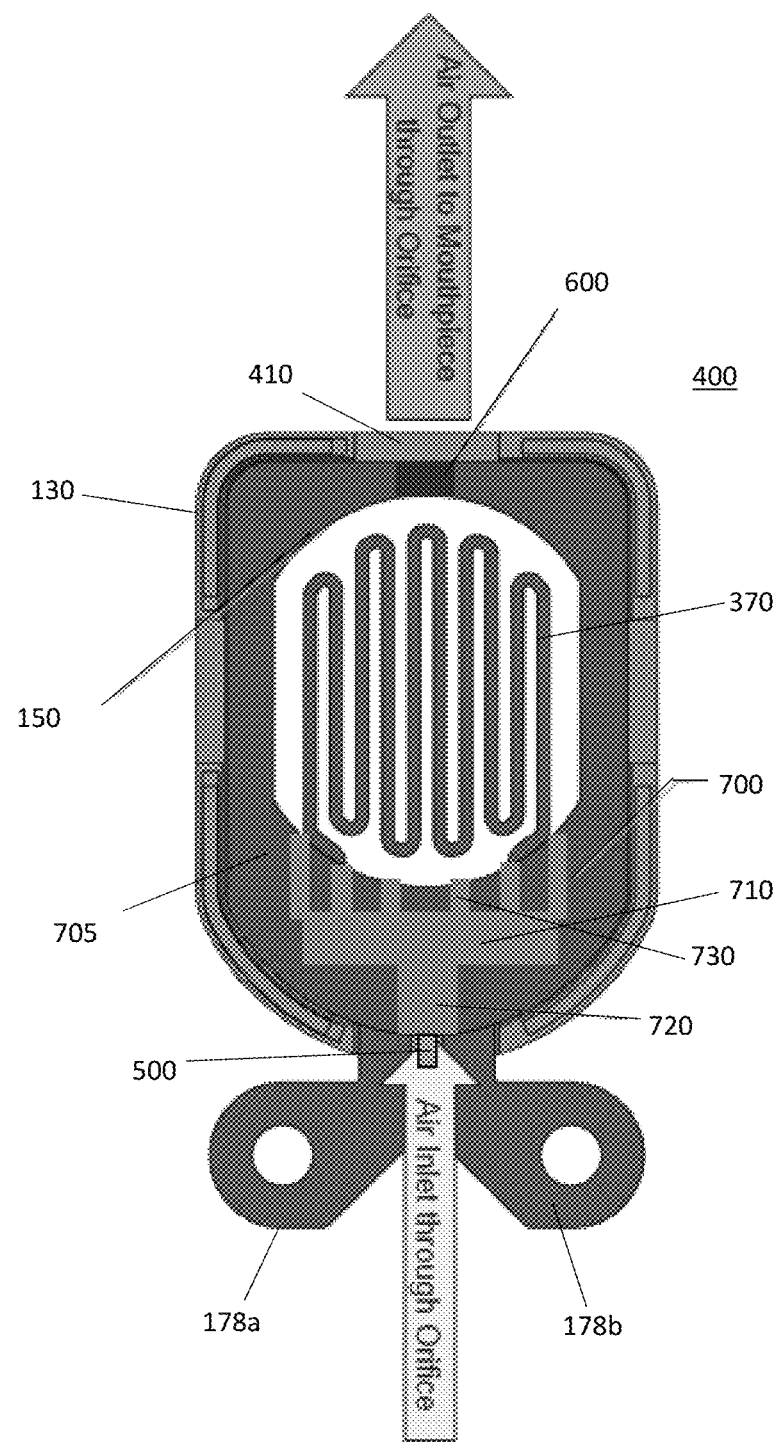

FIG. 7 is a view of the capsule of FIG. 4 illustrating an alternative airflow path therethrough according to at least one example embodiment.

In at least one example embodiment, as shown in FIG. 7, the capsule 400 is the same as the capsule 400 of FIG. 4-6 except that the capsule 400 includes a diffuser 700, but excludes the side air passages 500 aligned with the openings 410 described in FIGS. 5-6.

In at least one example embodiment, the capsule 400 includes only one air passage 500 between the tab portions 178a, 178b. The air passage 500 exits into the diffuser 700, which is configured to direct air and/or redistribute air from the at least one air passage 500 towards the outlet 600. The diffuser 700 includes at least one channel in a first face 705 of the inner frame 150. In at least one example embodiment, the diffuser 700 includes a main channel 720 extending from the at least one air passage 500. The main channel 720 extends in a generally longitudinal direction along a face of the inner frame 150. The diffuser 700 also includes at least one redistribution channel 710 extending from the main channel 720. The at least one redistribution channel 710 includes a lateral and/or perpendicular channel extending from and in fluid communication with the main channel 720. The diffuser 700 also includes at least one longitudinally extending secondary channel 730 extending from the redistribution channel 720. As shown in FIG. 7, the diffuser 700 includes six longitudinally extending secondary channels 730. In other example embodiments, the diffuser 700 may include between 2 and 20 secondary channels 710 (e.g., 4 to 18, 6 to 16, 8 to 14, or 10 to 12). In some example embodiments, the at least one secondary channel 730 is a straight channel. In at least one example embodiment, the secondary channel 730 may be angled channel with respect to the main channel 720. The secondary channels 730 may have any suitable shape, and may resemble tree branches extending from the main channel 720.

In at least one example embodiments, the main channel 720, the redistribution channel 710, and the at least one secondary channel 730 in the face of the inner frame 150 is about 0.1 mm to about 0.5 mm deep (e.g., about 0.2 mm to about 0.4 mm or about 0.25 mm to about 0.35 mm). Further, the capsule 400 is sealed, such the air flows in through the passage 500 through the diffuser 700, across the heater 370, and out through the outlet 600, such that the airflow pathway through the capsule 400 is longer than a thickness of the capsule.

Figure 8:
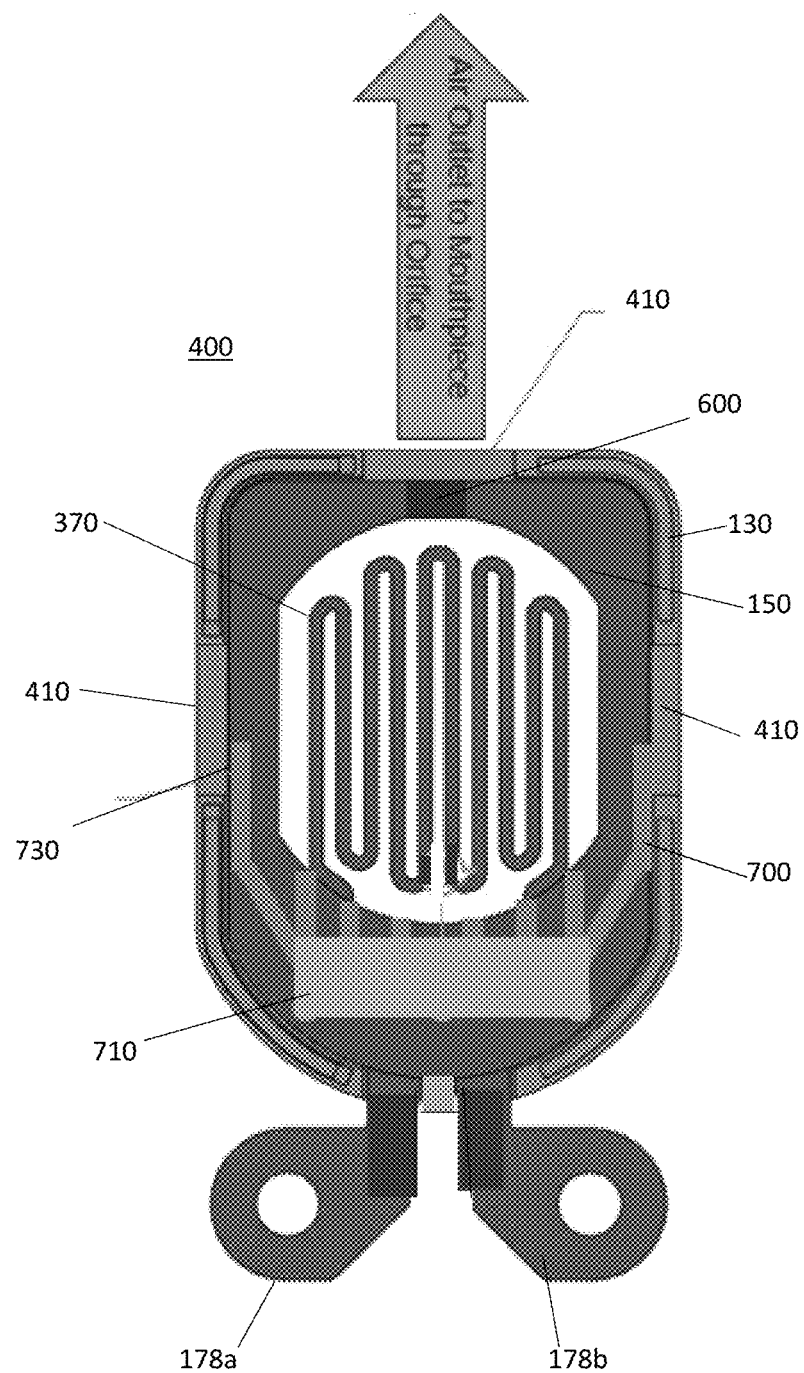

FIG. 8 is a view of the capsule of FIG. 4 illustrating airflow therethrough according to at least one example embodiment.

In at least one example embodiment, as shown in FIG. 8, the capsule is the same as the capsule 400 of FIG. 7 except that the diffuser 700 communicates only with the side openings 410 and the capsule 400 does not include an opening 410 between the tab portions 178a, 178b or air passages 500 through the inner frame 150.

As shown in FIG. 8, the diffuser 700 includes the redistribution channel 710 and the secondary channels 730. Air enters the capsule 400 via the side openings 410, travels through the secondary channel 730 adjacent the side openings, through the redistribution channel 710 to other branches of the diffuser 700, across the heater 370, and to the outlet 600. In at least one example embodiment, the channels 710, 730 are about 0.25 mm deep in the first face 705 of the inner frame 150. The airflow pathway through the capsule 400 is longer than a thickness of the capsule.

Figure 9:
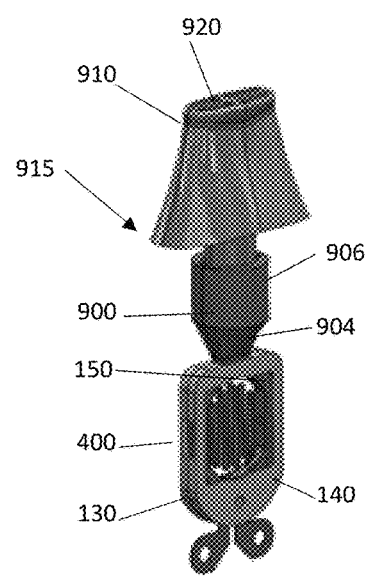

FIG. 9 is a perspective view of a capsule assembly including a capsule connected with a mouthpiece according to at least one example embodiment.

In at least one example embodiment, as shown in FIG. 9, a capsule assembly 915 includes the capsule of FIG. 4 and the inner frame 150 includes an extension portion 900 connected to a mouthpiece 910.

As shown in FIG. 9, the capsule 400 includes the inner frame 150, which includes the extension portion 900. The extension portion 900 and the inner frame 150 can be a single piece that is 3D printed or otherwise formed. The extension portion 900 includes a neck portion 904 and a body portion 906. The neck portion 904 may be V-shaped, while the body portion 906 may be generally circular in cross-section and have a diameter that is wider than the capsule 400. The neck portion 904 and the body portion 906 can be any suitable shape that is configured to connect with the mouthpiece 910.

In at least one example embodiment, the mouthpiece 910 may be any suitable mouthpiece such as the mouthpiece described in U.S. Pat. No. 10,064,432, the entire content of which is incorporated herein by reference. For example, the mouthpiece 910 may include at least one outlet 920. As shown, the mouthpiece 910 includes four outlets 920 and a portion of the mouthpiece 910 fits within the body 906 of the extension portion 900. In other example embodiments, the mouthpiece 910 may include one or more outlets and/or a portion of the mouthpiece 910 may surround the extension portion 900 of the inner frame 150. The first frame 130 and the second frame 140 fit around the inner frame 150 and a portion of the extension portion 900 that extends beyond the first and second frames 130, 140.

Figure 10:
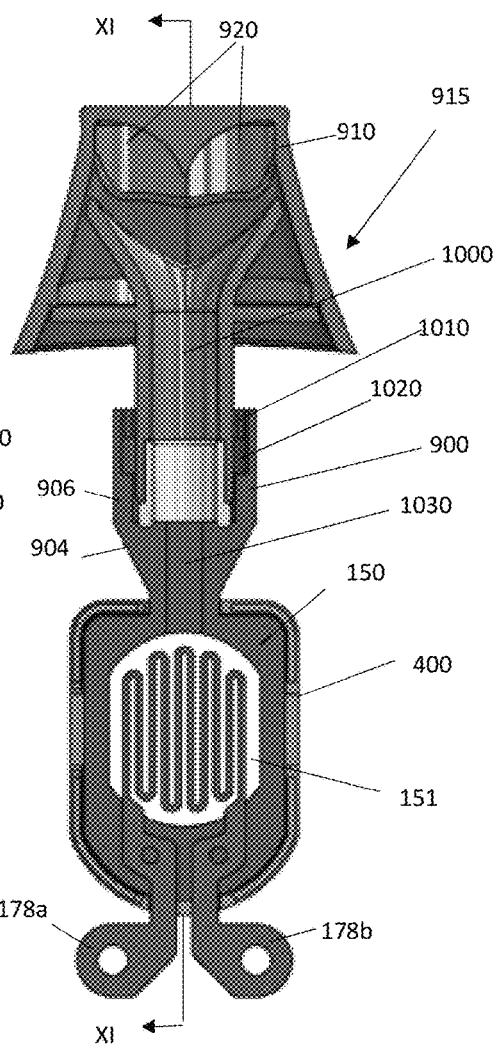

FIG. 10 is a side cross-sectional view of the capsule assembly of FIG. 9 according to at least one example embodiment.

In at least one example embodiment, as shown in FIG. 10, the capsule 400 and mouthpiece 910 are the same as shown in FIGS. 4 and 9, respectively, but alternative internal features are shown. As shown in FIG. 10, the extension portion 900 defines a chamber 1020. The chamber 1020 is configured to receive a base 1010 of the mouthpiece 910. The base 1010 of the mouthpiece 910 defines a passage 1000. The inner frame 150 and the extension portion 900 further define an extension channel 1030, which extends from the cavity 151 and through a length of the extension portion 900. The cavity 151 is in fluid communication with the passage 1000 and outlet 920 of the mouthpiece 910, such that aerosol and/or air exits the capsule 400 and mouthpiece via the outlets 920.

Figure 11:
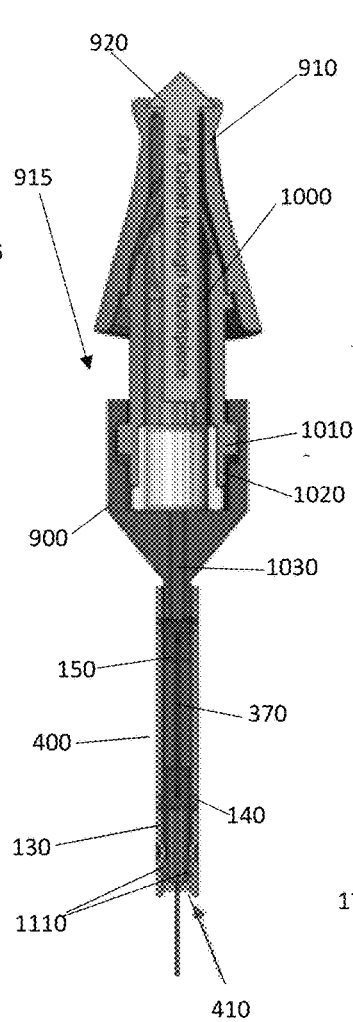

FIG. 11 is a side cross-sectional view along line XI-XI of the capsule assembly of FIG. 10 according to at least one example embodiment.

In at least one example embodiment, as shown in FIG. 11, the capsule assembly 915 including the capsule 400 and the mouthpiece 910 are the same as in FIGS. 9 and 10 except that the capsule 400 includes vents 1110 in communication with the opening 410. The inner frame 150 defines the vents 1110 on the first and second face thereof. The vents 1110 extend from the and are in fluid communication with the opening 410 adjacent the tab portions 178a, 178b, such that the air flows from the vents 1110 to the cavity 151 when a draw is taken on the mouthpiece 910. In at least one example embodiment, the vents 1110 may be molded into a surface of the inner frame 150. The vents 1110 may be about 10 microns deep and/or about 10 microns wide. In some example embodiments, a depth and/or a width of the vents 1110 may be adjusted so as to adjust an amount of air allowed to flow into the capsule 400. The vents 1110 may be designed so as to maintain the aerosol-forming substrate 160 within the capsule 400, while creating a comfortable draw for an adult consumer.

Figure 12:
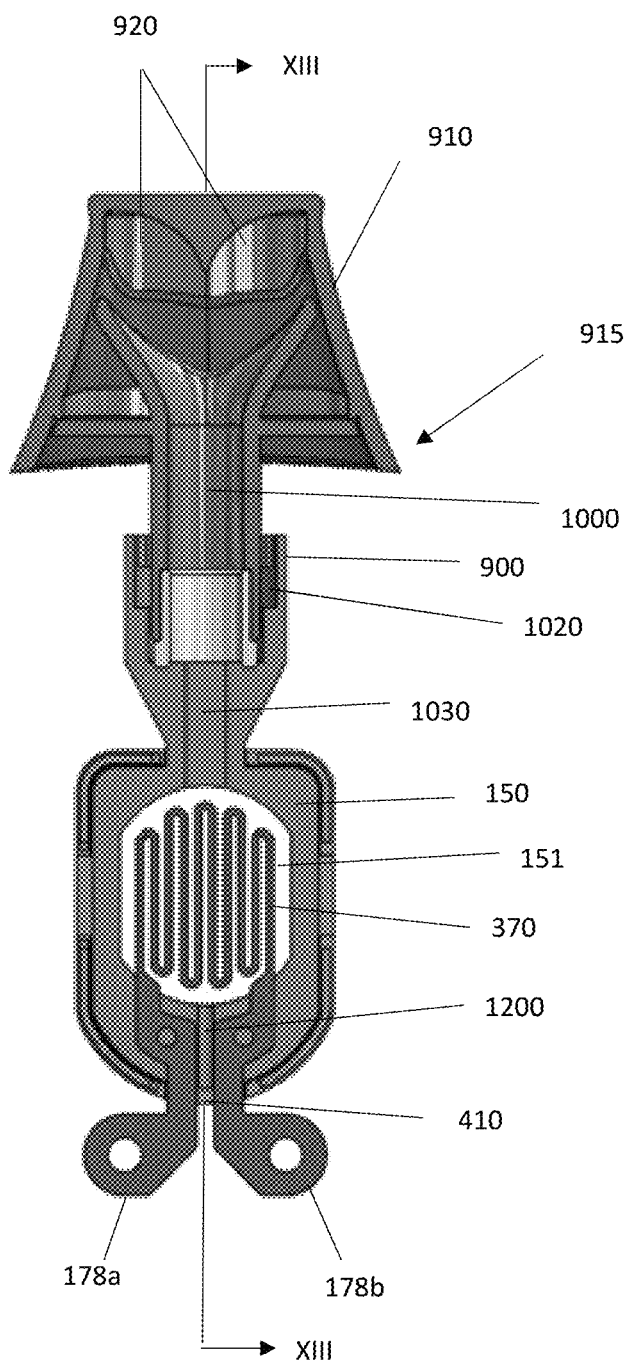

FIG. 12 is a side cross-sectional view of the assembly of FIG. 9 according to at least one example embodiment.

In at least one example embodiment, as shown in FIG. 12, the capsule assembly 915 is the same as in FIG. 4 and FIGS. 9-10, except that instead of the vents 1110 of FIG. 11, a channel 1200 is defined by and extends through a portion of the inner frame 150. As shown in FIG. 12, air enters the capsule 400 via the opening 410, passes through the channel 1200 within the inner frame 150 into the cavity 151, flows through the extension channel 1030, into the passage 1000 of the mouthpiece 910, and out of the capsule assembly 915 via the outlets 920 of the mouthpiece 910.

Figure 13:
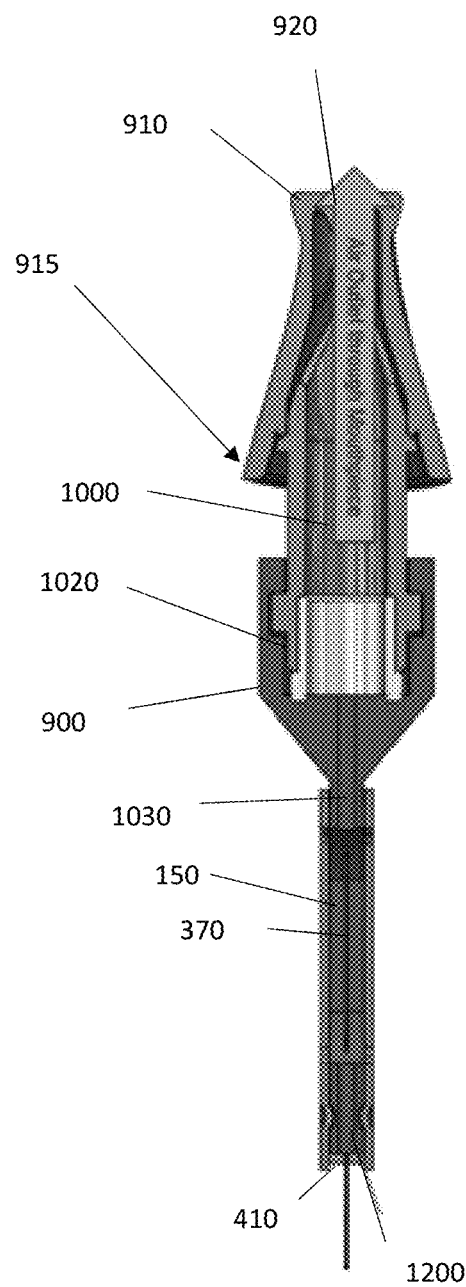

FIG. 13 is a side cross-sectional view along line XIII-XIII of the capsule assembly of FIG. 12 according to at least one example embodiment.

In at least one example embodiment as shown in FIG. 13, the capsule assembly 915 is same as in FIG. 12, but the channel 1200 and the vents 1110 are shown in cross-section.

Figure 14:
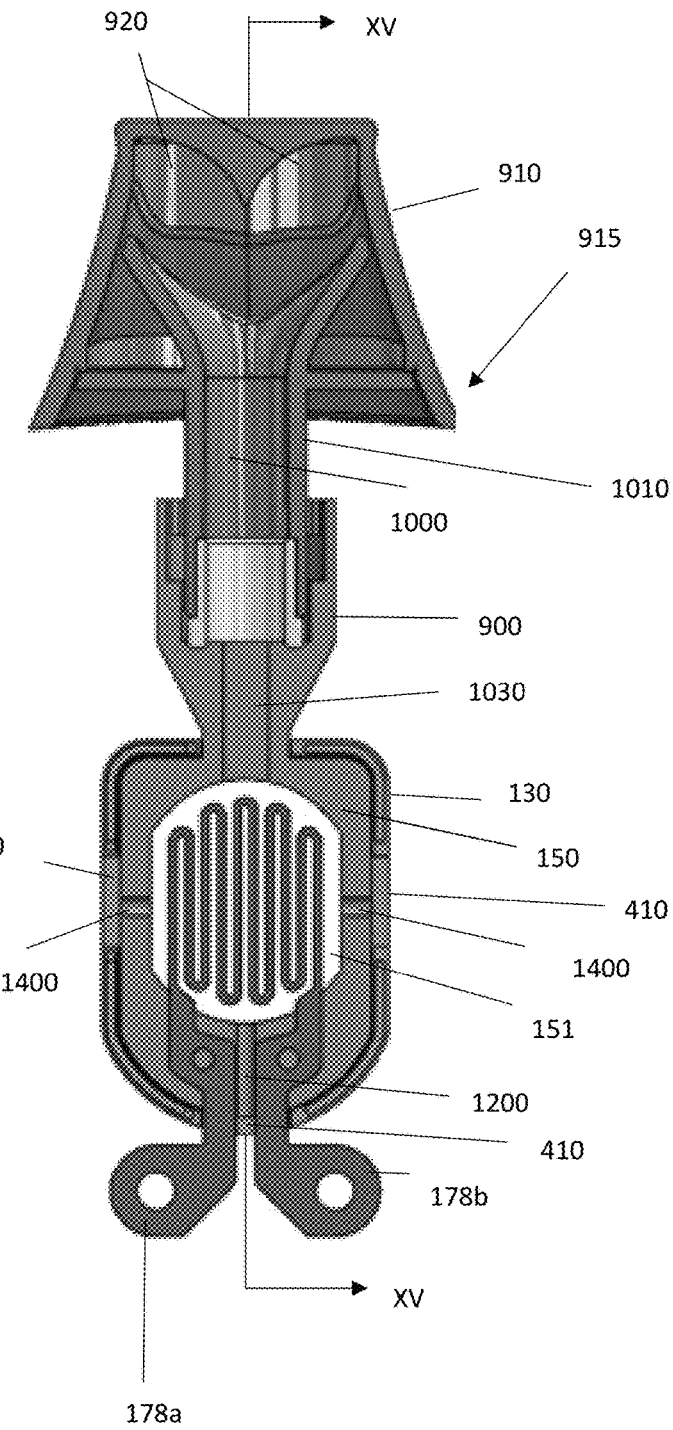

FIG. 14 is a side cross-sectional view of the capsule assembly of FIG. 9 according to at least one example embodiment.

Figure 15:
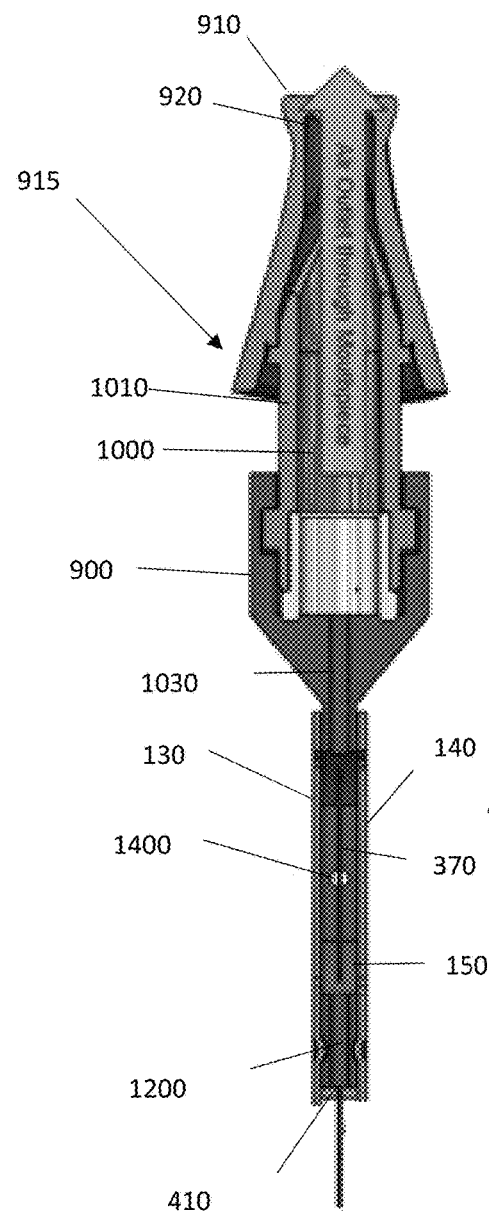

FIG. 15 is a side cross-sectional view along line XV-XV of the capsule assembly of FIG. 14 according to at least one example embodiment.

In at least one example embodiment, as shown in FIGS. 14 and 15, the capsule assembly is the same as in FIG. 9 except that the capsule 400 (which is the same as in FIG. 4) includes side channels 1400, the central channel 1200 in the inner frame 150 (as shown and described with respect to FIGS. 12-13), and the mouthpiece 910 of FIGS. 9 and 10.

As shown in FIGS. 14 and 15, the capsule 400 includes side channels 1400 that align with the openings 410 established between the first frame 130 and the second frame 140. The capsule 400 also include the central channel 1200 that aligns with the opening 410 established between the first frame 130 and the second frame 140. When a draw is taken on the mouthpiece 910, air is pulled into the capsule 400 via the openings 410, through the side channels 1400 and the central channel 1200, into the cavity 151, into the extension channel 1030, into the passage 1000 and out of the mouthpiece 910 via the outlets 920.

In at least one example embodiment, the central channel 1200 may have a diameter of about 0.5 mm to about 1.5. The side channels 1400 may also have a diameter of about 0.5 mm to about 1.5 mm. For example, the central channel 1200 and the side channels 1400 may each have a diameter of about 1.0 mm.

Figure 16:
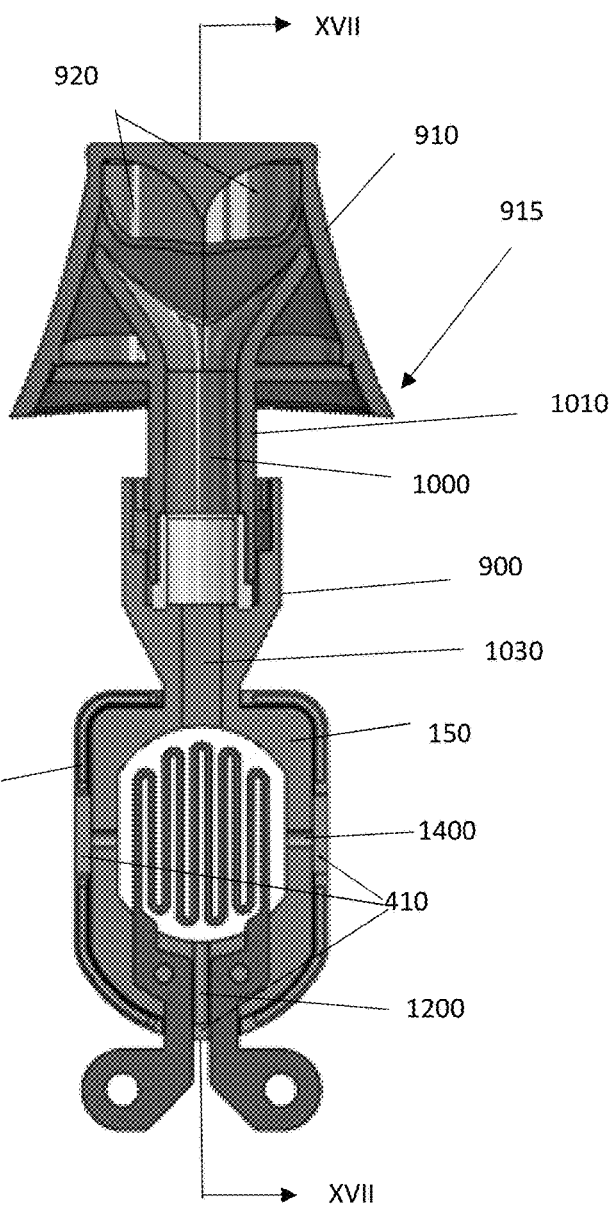

FIG. 16 is a side cross-sectional view of the capsule assembly of FIG. 9 according to at least one example embodiment.

Figure 17:
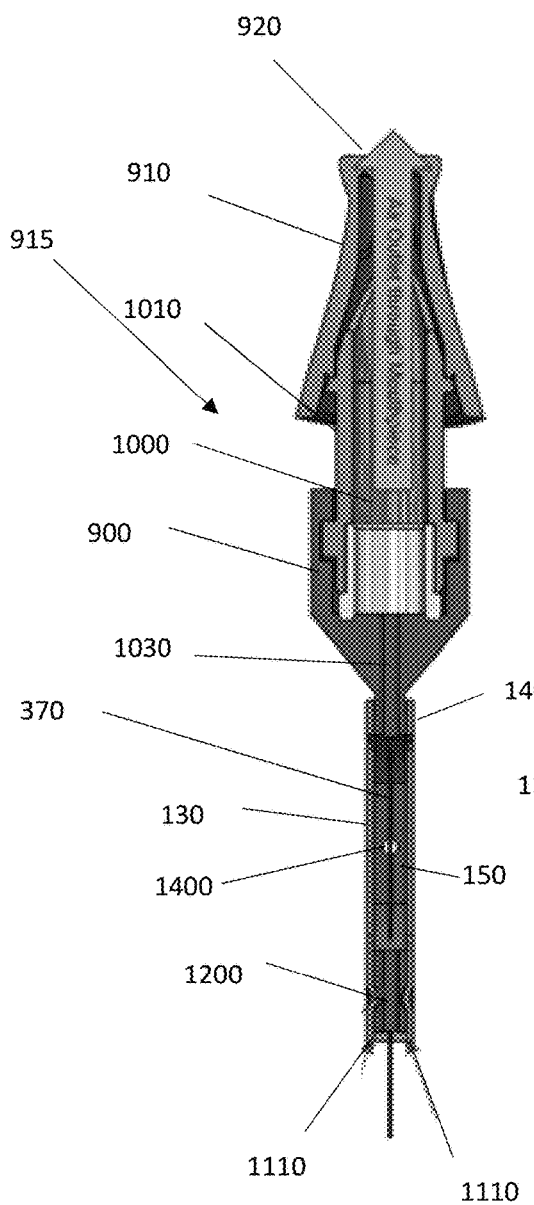

FIG. 17 is a side cross-sectional view along line XVII-XVII of the capsule assembly of FIG. 16 according to at least one example embodiment.

In at least one example embodiment, as shown in FIGS. 16 and 17, the capsule assembly is the same as the capsule assembly 915 of FIGS. 14 and 15 and includes the capsule 400, which is the same as the capsule of FIG. 4 except that the capsule 400 also includes two vents 1110 along faces of the inner frame 150 as shown and described with respect to FIG. 11. When a draw is taken on the mouthpiece 910, air is drawn into the capsule 400 through the openings 410 in the bottom portion and sides of the capsule 400, through the vents 1110, central channel 1200, and the side channels 1400, into the cavity 151, through the extension channel 1030, into the passage 1000 of the mouthpiece, and out of the capsule assembly via the outlets 920.

In at least one example embodiment, the central channel 1200 and the side channels 1400 each have a diameter of about 1 mm.

FIG. 18 is a side perspective view of a capsule assembly including a capsule enclosed in a capsule enclosure and connected to a mouthpiece according to at least one example embodiment.

FIG. 19 is a side cross-sectional view along line XIX-XIX of the capsule assembly of FIG. 18 according to at least one example embodiment.

In at least one example embodiment, as shown in FIGS. 18 and 19, the capsule assembly 1800 can include the capsule 400 of FIG. 4, the mouthpiece of FIG. 9, and further including a capsule enclosure 1810 in lieu of the extension portion shown and described in FIGS. 9-17.

As shown in FIGS. 18 and 19, the capsule enclosure 1810 substantially encloses the capsule 400 so as to seal the capsule 400 (shown in FIG. 19) and force airflow across and/or along the heater 370 within the capsule 400. As shown in FIGS. 18 and 19, the capsule enclosure 1810 includes a first body 1820 and a second body 1830. The first body 1820 and the second body 1830 may be 3D printed or molded and connected together around portions of the capsule 400 and the mouthpiece 910. The connection between the first body 1820 and the second body 1830 may be made with any suitable connection including rubber bands, adhesives, and/or mechanical connections formed into the first body 1820 and/or the second body 1830.

In at least one example embodiment, the capsule enclosure 1810 defines a passageway 1900 therethrough. As shown in FIG. 19, the passageway 1900 includes a first passageway section 1920 extending through a portion of the first body 1820 and a second passageway section 1930 extending through a portion of the second body 1830. Further, as shown in FIG. 19, the second passageway section 1930 may include an inlet 1940 through which air enters when a draw is taken on the mouthpiece 910. The air travels through the inlet 1940 to and through the second passageway section 1930 to the capsule 400. The air may enter the capsule 400 at a top thereof. At the capsule 400, the air flows through the first permeable or impermeable structure, which in this example embodiment, is permeable. The air then travels through and/or across the aerosol-forming substrate (shown and described with respect to FIGS. 2A and 2B) and across the heater 370. As shown, the airflow is generally longitudinal and/or diagonal across the heater 370, and exits the capsule 400 at a bottom thereof. The air exits the capsule 400 via the second permeable or impermeable structure 120, which in this example embodiment, is permeable. The air travels through the second passageway section 1930 through the capsule enclosure exit 1950, into the passage 1000 of the mouthpiece 910 and out of the capsule assembly 1800 via the outlets 920. The airflow pathway through the capsule 400 is longer than a thickness of the capsule.

Figure 23:
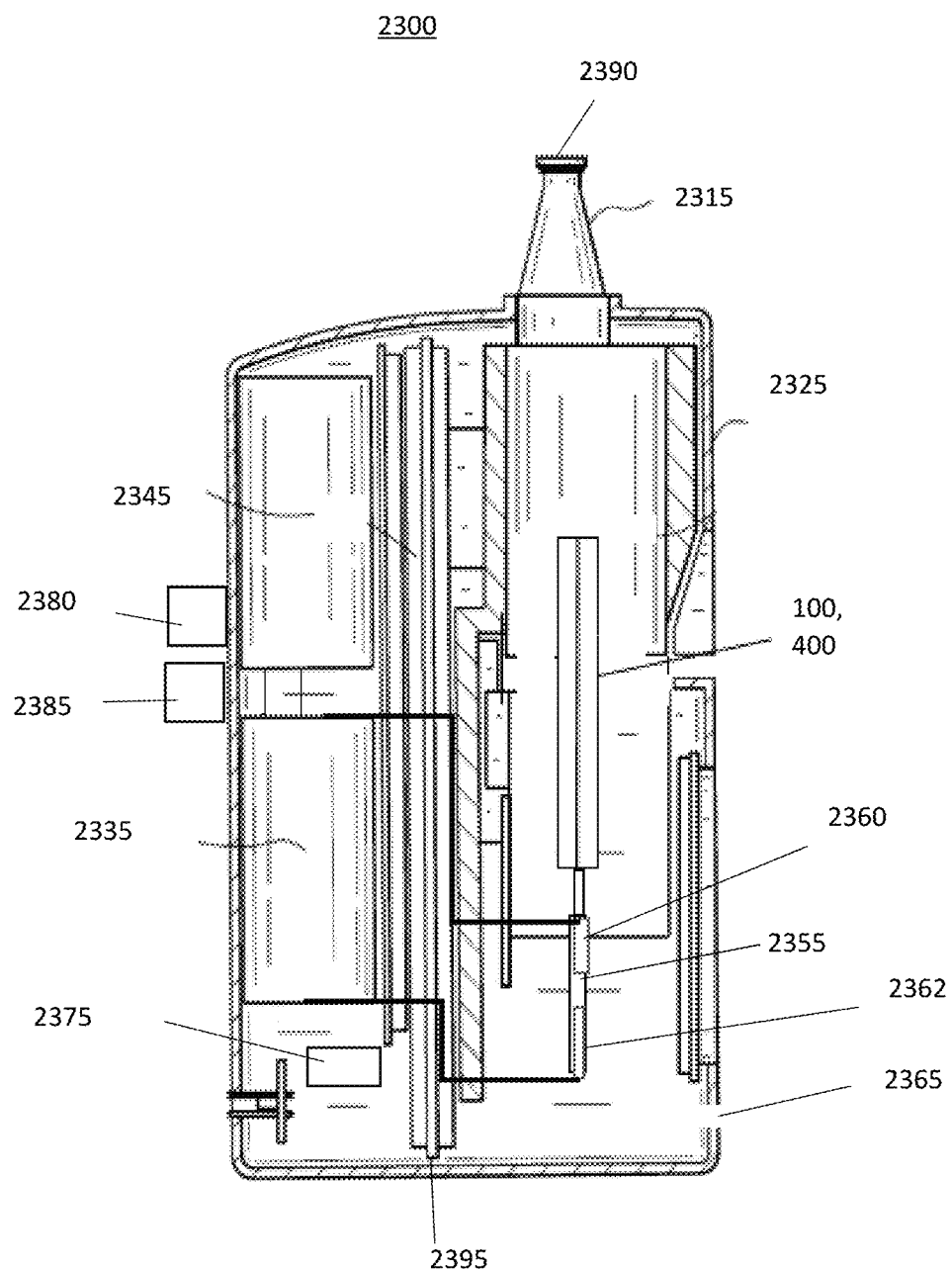

In at least one example embodiment, as shown in FIG. 19, the tab portions 178a, 178b of the capsule 400 extend out of the capsule enclosure 1810 so as to facilitate electrical connection with a power supply and/or control circuitry in an aerosol-generating device as described further with respect to FIG. 23.

In at least one example embodiment, while the mouthpiece 910 is shown centered on the capsule assembly 1800, the mouthpiece 910 could be arranged off-center so as to avoid and/or reduce the number of turns in the passageway 1900.

Further, the inlet 1940 could be connected to a flow sensor or adjacent area via tubing if desired.

Figure 20:
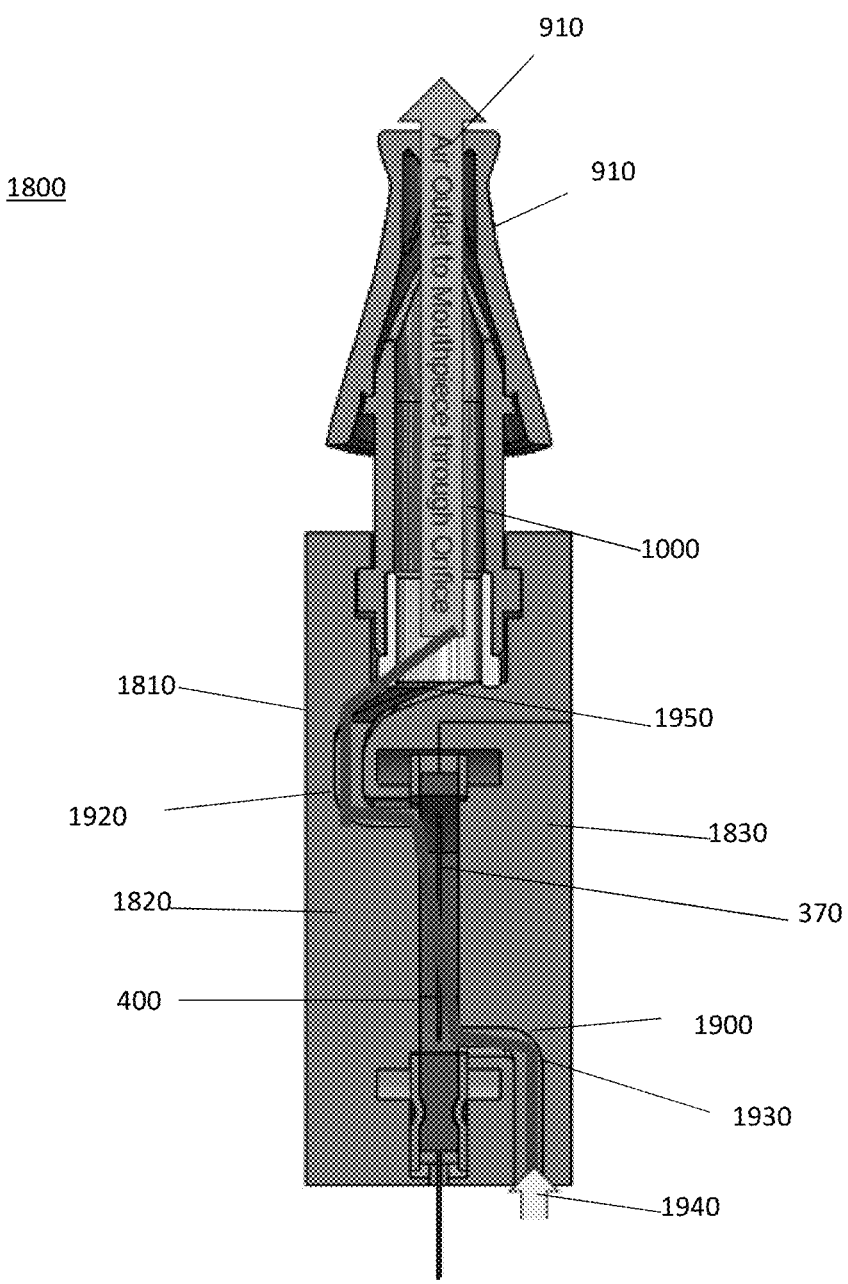

FIG. 20 is a side cross-sectional view of the capsule assembly of FIG. 18 according to at least one example embodiment.

In at least one example embodiment, as shown in FIG. 20, the capsule assembly 1800 is the same as in FIGS. 18 and 19, except that the passageway 1900 is arranged such that air enters the capsule 400 at a bottom thereof and exits at a top thereof. The air travels generally longitudinally and/or diagonally across the capsule so as to prolong contact with the aerosol-forming substrate and/or heater 370.

Figure 21:
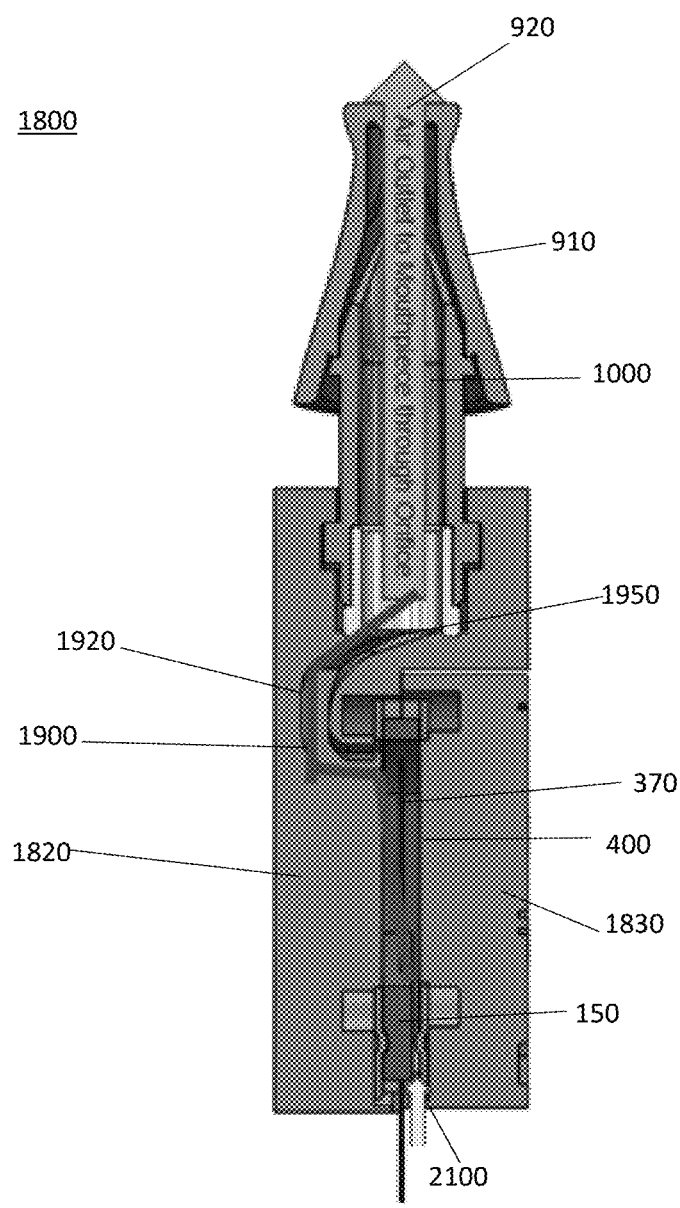

FIG. 21 is a side cross-sectional view of the capsule assembly of FIG. 18 according to at least one example embodiment.

In at least one example embodiment, as shown in FIG. 21, the capsule assembly 1800 is the same as in FIG. 18 except that the capsule 400 includes a vent 2100 on a first face of the inner frame 150 and the passageway 1900 excludes the second passageway section 1930 and inlet 1940 thereto.

As shown in FIG. 21, air enters the capsule 400 via the vent 2100 and then passes longitudinally and/or diagonally across the aerosol-forming substrate and/or heater 370 before passing into the first passageway section 1920, the outlet 1950 and into the passage 1000 of the mouthpiece 910. The airflow pathway through the capsule 400 is longer than a thickness of the capsule.

Figure 22:
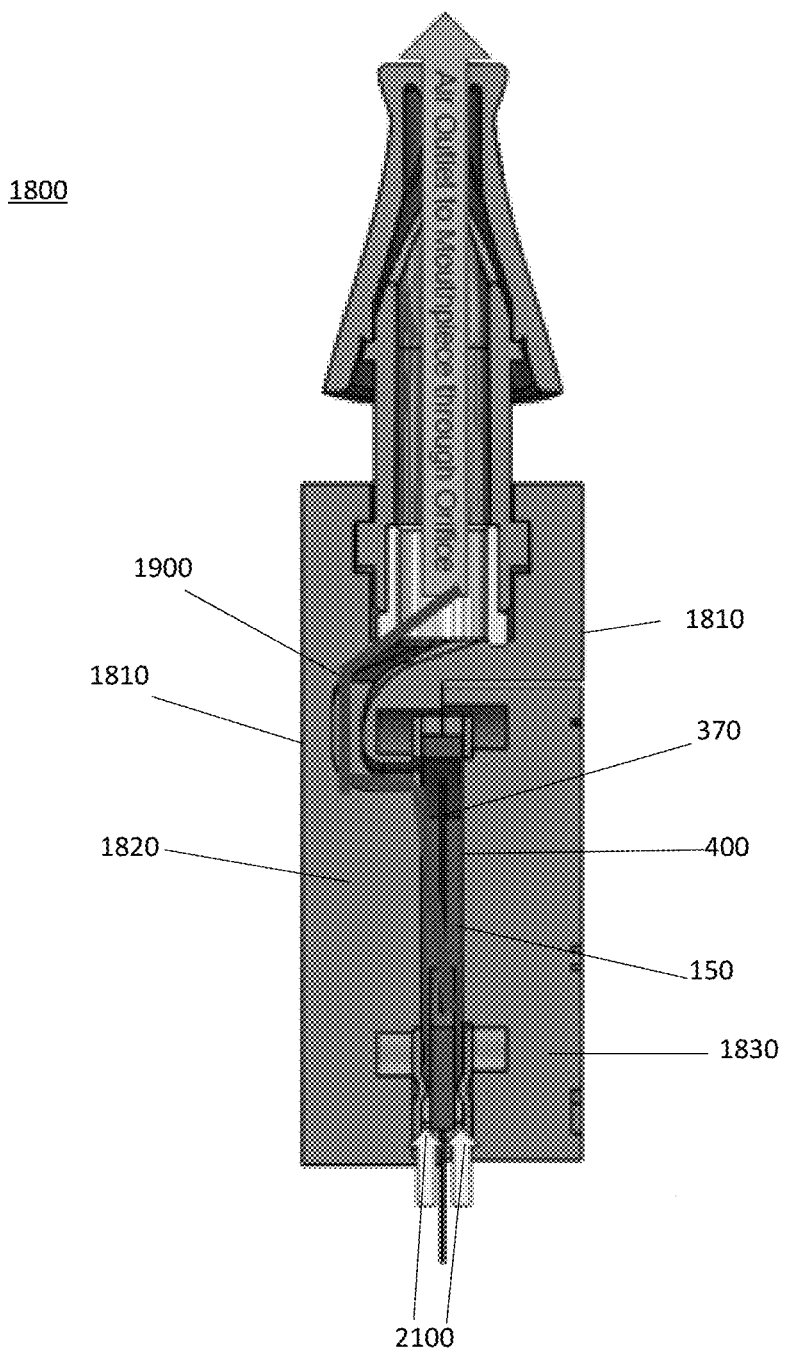

FIG. 22 is a side cross-sectional view of the capsule assembly of FIG. 18 according to at least one example embodiment.

In at least one example embodiment, as shown in FIG. 22, the capsule assembly is the same as that of FIG. 21, except that the capsule 400 includes two vents 2100. As shown, a first vent 2100a is on a first face and a second vent 2100b is on a second face of the inner frame 150. Air enters the capsule assembly 1800 via the vents 2100a, 2100b.

FIG. 23 is a schematic illustration of an aerosol generating device for use with a capsule according to at least one example embodiment.

In at least one example embodiment, as shown in FIG. 23, an aerosol-generating device 2300 (e.g., heat-not-burn aerosol-generating device) includes a mouthpiece 2315 and a device body 2325. A power source 2335 and control circuitry 2345 may be disposed within the device body 2325 of the aerosol-generating device 2300. At least one air inlet 2365 may be defined in a wall of the device body 2325. The power source 2335 may include one or more batteries (e.g., rechargeable dual battery arrangement), such as Lithium ion batteries. The aerosol-generating device 2300 is configured to receive a capsule 100, 400 and/or capsule assembly as described herein, which may be as described in connection with any of the embodiments herein. The aerosol-generating device 2300 also includes an engagement assembly 2355 configured to electrically contact the capsule 100, 400. The engagement assembly 2355 may include a first electrode 2360 and a second electrode 2362 configured to electrically contact a first end section and a second end section, respectively, of a heater of the capsule.

After the capsule 100, 400 is inserted into the aerosol-generating device 2300, the control circuitry 2345 may instruct the power source 2335 to supply an electric current between the first electrode 2360 and the second electrode 2362 of the engagement assembly 2355. The supply of current from the power source 2335 may be in response to a manual operation (e.g., button-activation) or an automatic operation (e.g., puff-activation). As a result of the current, the capsule 100, 400 may be heated to generate an aerosol. In addition, the change in resistance of the heater may be used to monitor and control the aerosolization temperature. The aerosol generated may be drawn from the aerosol-generating device 2300 via the mouthpiece 2315.

In at least one example embodiment, upon activating the aerosol-generating device 2300, the capsule 100, 400 within the device body 2325 may be heated to generate an aerosol. In at least one example embodiment, activation of the aerosol-generating device 2300 may be triggered by the detection of an air flow by a sensor 2375 and/or the generation of a signal associate with the pressing of a first button 2380 and/or a second button 2385. With regard to the detection of an air flow, a draw or application of negative pressure on the aerosol outlet 2390 of the mouthpiece 2315 will pull ambient air into the device body 2325 via the air inlet 2365. Once inside the device body 2325, the air travels through an inlet channel 2395 and is detected by the sensor 2375. A portion of the air also enters the capsule 100, 400 as described herein.

The detection of the air flow by the sensor 2375 causes the control circuitry 2345 to instruct the power source 2335 to supply an electric current to the capsule 100, 400 via the first end section 172 and the second end section 176 of the heater 170, 370 (as described herein). As a result, the temperature of the intermediate section 174 of the heater 170, 370 will increase which, in turn, will cause the temperature of the aerosol-forming substrate (e.g., aerosol-forming substrate 160) to increase such that volatiles are released by the aerosol-forming substrate 160 to produce an aerosol. The aerosol produced will be entrained by the air flowing through the capsule 100, 400. In particular, the aerosol produced will pass through the capsule 100, 400 before exiting the aerosol-generating device 2300 from the aerosol outlet 2390 of the mouthpiece 2315.

The processing circuitry (control circuitry) may be hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

Additional details of the capsule 100, 400 and the aerosol-generating device 2300, including the mouthpiece 2315, the device body 325, the power source 2335, the control circuitry 2345, the electrodes may be found in U.S. application Ser. No. 15/845,501, filed Dec. 18, 2017, titled "VAPORIZING DEVICES AND METHODS FOR DELIVERING A COMPOUND USING THE SAME,", the disclosure of which is incorporated herein in its entirety by reference. The capsule, aerosol-forming substrate, and related aspects discussed herein are also described in more detail in U.S. application Ser. No. 16/252,951, filed Jan. 21, 2019, titled "CAPSULE, HEAT-NOT-BURN (HNB) AEROSOL-GENERATING DEVICES, AND METHODS OF GENERATING AN AEROSOL,", the disclosure of which is incorporated herein in its entirety by reference.

Additional details of the substrates, capsules, devices, and methods discussed herein may also be found in U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL,"; U.S. application Ser. No. 16/252,951, filed Jan. 21, 2019, titled "CAPSULES, HEAT-NOT-BURN (HNB) AEROSOL-GENERATING DEVICES, AND METHODS OF GENERATING AN AEROSOL,"; U.S. application Ser. No. 15/845,501, filed Dec. 18, 2017, titled "VAPORIZING DEVICES AND METHODS FOR DELIVERING A COMPOUND USING THE SAME,"; U.S. application Ser. No. 15/559,308, filed Sep. 18, 2017, titled "VAPORIZER FOR VAPORIZING AN ACTIVE INGREDIENT,"; and U.S. application Ser. No. 16/909,131, filed Jun. 23, 2020, titled "CAPSULES INCLUDING INTERNAL HEATERS, HEAT-NOT-BURN (HNB) AEROSOL-GENERATING DEVICES, AND METHODS OF GENERATING AN AEROSOL,", the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
   a housing defining at least one air inlet and at least one air outlet, the housing including,
      a first frame defining a cavity, the first frame being an inner frame, the first frame including,
         a first face,
         a second face,
         a first end surface,
         a second end surface,
         a first side, and
         a second side, the at least one air inlet extending through the first end surface of the first frame, the at least one air inlet opposite the at least one air outlet;
   an aerosol-forming substrate at least partially within the cavity; and
   a heater supported by the first frame and extending across at least a portion of the cavity,
   the at least one air inlet, the cavity, and the at least one air outlet collectively forming at least one airflow pathway through the capsule, the airflow pathway being longer than a thickness of the capsule, such that air flows longitudinally across the heater and the aerosol-forming substrate so as to prolong contact with the heater and the aerosol-forming substrate, the at least one air inlet including a first air inlet and a second air inlet, the first air inlet extending through the first side and the second air inlet extending through the first end surface of the inner frame, and the at least one air outlet extending through the second end surface of the inner frame.

2. The capsule of claim 1, wherein the aerosol-forming substrate includes a plant material.

3. The capsule of claim 2, wherein the plant material includes tobacco.

4. The capsule of claim 1, further comprising:

a diffuser configured to redistribute air from the at least one air inlet towards the at least one air outlet, the diffuser including at least one channel on the first face of the inner frame.

5. A capsule for an aerosol-generating device, comprising:

a housing defining at least one air inlet and at least one air outlet, the housing including, a first frame defining a cavity, the first frame being an inner frame, the first frame including, a first face, a second face, a first end surface, a second end surface, a first side, and a second side, the at least one air inlet extending through the first end surface of the first frame, the at least one air inlet opposite the at least one air outlet;

an aerosol-forming substrate at least partially within the cavity; and a heater supported by the first frame and extending across at least a portion of the cavity, the at least one air inlet, the cavity, and the at least one air outlet collectively forming at least one airflow pathway through the capsule, the airflow pathway being longer than a thickness of the capsule, such that air flows longitudinally across the heater and the aerosol-forming substrate so as to prolong contact with the heater and the aerosol-forming substrate; and a diffuser configured to redistribute air from the at least one air inlet towards the at least one air outlet, the diffuser including, a main channel extending longitudinally from the at least one air inlet, and at least one secondary channel in fluid communication with the main channel.

6. The capsule of claim 5, wherein the at least one secondary channel includes at least one parallel channel parallel to the main channel and at least one angled channel extending at an angle with respect to the main channel.

7. The capsule of claim 1, wherein the heater is sinuously shaped.

8. A capsule assembly for an aerosol-generating device, comprising:

a capsule including, a housing including, a first frame defining a cavity, the first frame being an inner frame, the first frame including, a first face, a second face, a first end surface, a second end surface, a first side, and a second side;

an aerosol-forming substrate at least partially within the cavity; and a heater supported by the inner frame and extending across at least a portion of the cavity; and a capsule enclosure surrounding at least a portion of the housing, the capsule enclosure defining at least one air inlet and at least air outlet, the at least one air inlet extending through the first end surface of the first frame, the at least one air inlet opposite the at least one air outlet, the at least one air inlet, the cavity, and the at least one air outlet collectively forming at least one airflow pathway through the capsule assembly, the airflow pathway being longer than a thickness of the capsule, such that air flows longitudinally across the heater and the aerosol-forming substrate so as to prolong contact with the heater and the aerosol-forming substrate, the at least one air inlet including a first air inlet and a second air inlet, the first air inlet extending through the first side and the second air inlet extending through the first end surface of the inner frame, and the at least one air outlet extending through the second end surface of the inner frame.

9. The capsule assembly of claim 8, wherein the capsule enclosure further comprises:

a capsule enclosure airflow channel extending between the at least one air inlet and the at least one air outlet, the capsule enclosure airflow channel defining a portion of the at least one airflow pathway.

10. The capsule assembly of claim 8, wherein the at least one airflow pathway extends diagonally across at least a portion of the cavity in the first frame.

11. The capsule assembly of claim 8, wherein the at least one airflow pathway extends diagonally across at least a portion of the heater and the aerosol-forming substrate.

12. An aerosol-generating device comprising:

a device body configured to receive a capsule, the capsule including, a housing including, a first frame defining a cavity, at least one air inlet, and at least one air outlet, the first frame being an inner frame, the first frame including, a first face, a second face, a first end surface, a second end surface, a first side, and a second side, the at least one air inlet extending through the first end surface of the first frame, the at least one air inlet opposite the at least one air outlet, an aerosol-forming substrate at least partially within the cavity, and a heater supported by the first frame and extending across at least a portion of the cavity, the at least one air inlet, the cavity, and the at least one air outlet collectively forming at least one airflow pathway through the capsule, the airflow pathway being longer than a thickness of the capsule, such that air flows longitudinally across the heater and the aerosol-forming substrate so as to prolong contact with the heater and the aerosol-forming substrate, the at least one air inlet including a first air inlet and a second air inlet, the first air inlet extending through the first side and the second air inlet extending through the first end surface of the inner frame, and the at least one air outlet extending through the second end surface of the inner frame;

a plurality of electrodes within the device body and configured to electrically contact the heater of the capsule; and a power source configured to supply an electric current to the heater of the capsule via the plurality of electrodes.

13. The aerosol-generating device of claim 12, wherein the aerosol-forming substrate includes a plant material.

14. The aerosol-generating device of claim 13, wherein the plant material includes tobacco.

15. The aerosol-generating device of claim 13, wherein the capsule further comprises:

a diffuser configured to redistribute air from the at least one air inlet towards the at least one air outlet, the diffuser including at least one channel on the first face of the inner frame.

16. An aerosol-generating device comprising:

a device body configured to receive a capsule, the capsule including,
  a housing including,
    a first frame defining a cavity, at least one air inlet, and at least one air outlet, the first frame being an inner frame, the first frame including,
      a first face,
      a second face,
      a first end surface,
      a second end surface,
      a first side, and
      a second side, the at least one air inlet extending through the first end surface of the first frame, the at least one air inlet opposite the at least one air outlet,
  an aerosol-forming substrate at least partially within the cavity,
  a heater supported by the first frame and extending across at least a portion of the cavity, the at least one air inlet, the cavity, and the at least one air outlet collectively forming at least one airflow pathway through the capsule, the airflow pathway being longer than a thickness of the capsule, such that air flows longitudinally across the heater and the aerosol-forming substrate so as to prolong contact with the heater and the aerosol-forming substrate, and a diffuser configured to redistribute air from the at least one air inlet towards the at least one air outlet, the diffuser including,
  a main channel extending longitudinally from the at least one air inlet; and
  at least one secondary channel in fluid communication with the main channel;

a plurality of electrodes within the device body and configured to electrically contact the heater of the capsule; and a power source configured to supply an electric current to the heater of the capsule via the plurality of electrodes.

17. The aerosol-generating device of claim 16, wherein the at least one secondary channel includes at least one parallel channel parallel to the main channel and at least one angled channel extending at an angle with respect to the main channel.

18. A method of generating an aerosol comprising:

electrically contacting a plurality of electrodes with a capsule, the capsule including a housing including an inner frame, the inner frame including a first face, a second face, a first end surface, a second end surface, a first side, and a second side, the housing defining a cavity, at least one air inlet, and at least one air outlet, the at least one air inlet extending through the first end surface of the inner frame, the at least one air inlet opposite the at least one air outlet, the at least one air inlet including a first air inlet and a second air inlet, the first air inlet extending through the first side and the second air inlet extending through the first end surface of the inner frame, and the at least one air outlet extending through the second end surface of the inner frame, an aerosol-forming substrate at least partially within the cavity, a heater supported by the inner frame and extending across at least a portion of the cavity, the at least one air outlet, the at least one air inlet, the cavity, and the at least one air outlet collectively forming at least one airflow pathway through the capsule, the airflow pathway being longer than a thickness of the capsule, such that air flows longitudinally across the heater and the aerosol-forming substrate so as to prolong contact with the heater and the aerosol-forming substrate; and supplying an electric current to the heater of the capsule via the plurality of electrodes.

* * * * *